United States Patent
Sano et al.

(10) Patent No.: US 7,685,886 B2
(45) Date of Patent: Mar. 30, 2010

(54) CONVEXO CONCAVE AMPLIFYING DEVICE AND CONVEXO CONCAVE DETECTING METHOD BY USE THEREOF, DEFORMATION SENSING DEVICE AND CONVEXO CONCAVE DETECTING METHOD BY USE THEREOF, AND CONVEXO CONCAVE POSITION EXHIBITING DEVICE AND CONVEXO CONCAVE POSITION EXHIBITING METHOD

(75) Inventors: Akihito Sano, Gifu-ken (JP); Hiromi Mochiyama, Nagoya (JP); Naoyuki Takesue, Nagoya (JP); Ryo Kikuuwe, Nagoya (JP); Hideo Fujimoto, Nagoya (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 116 days.

(21) Appl. No.: 10/584,627

(22) PCT Filed: Dec. 27, 2004

(86) PCT No.: PCT/JP2004/019828

§ 371 (c)(1),
(2), (4) Date: Jun. 26, 2006

(87) PCT Pub. No.: WO2005/064299

PCT Pub. Date: Jul. 14, 2005

(65) Prior Publication Data
US 2007/0186642 A1 Aug. 16, 2007

(30) Foreign Application Priority Data
Dec. 26, 2003 (JP) .................. 2003-435068
Mar. 31, 2004 (JP) .................. 2004-106923

(51) Int. Cl.
*G01N 3/20* (2006.01)

(52) U.S. Cl. .................. 73/849; 73/862.391
(58) Field of Classification Search .......... 73/172, 73/849
See application file for complete search history.

(56) References Cited

U.S. PATENT DOCUMENTS 4,657,021 A  4/1987  Perry et al.

(Continued)

FOREIGN PATENT DOCUMENTS

JP   39-29494   12/1939

(Continued)

*Primary Examiner*—Hezron Williams
*Assistant Examiner*—Mark Shabman
(74) *Attorney, Agent, or Firm*—Finnegan, Henderson, Farabow, Garrett & Dunner, LLP

(57) ABSTRACT

A convexo concave amplifying device for exhibiting a convexo concave by amplifying a sense of a convexo concave of an object, comprising a sensing member and an exhibiting member. The sensing member 101 comprises a flexible sheet able to contact with the surface of the object O and to deform along the surface of the object. The exhibiting member 120 that is formed on a surface of the flexible sheet and has a deformation resistance smaller than that of the flexible sheet in at least one of directions orthogonal to a direction of thickness of the flexible sheet. With such construction, the object convexo concave can be amplified and exhibited.

A deformation sensing device for sensing a deformation thereof comprising a capsule deformable by stress, a viscous fluid F contained in the capsule, and a relative movement sensing member that is disposed inside of the capsule and senses a relative movement against the viscous fluid. With such construction, property of the object such as the convexo concave or the stress can be detected.

14 Claims, 10 Drawing Sheets

U.S. PATENT DOCUMENTS

| | | |
|---|---|---|
| 4,793,354 A | 12/1988 | Wright et al. |
| 5,946,727 A | 9/1999 | Wright et al. |
| 5,989,199 A | 11/1999 | Cundari et al. |
| 6,179,790 B1 | 1/2001 | Cundari et al. |
| 6,445,284 B1 * | 9/2002 | Cruz-Hernandez et al. .................. 340/407.1 |

FOREIGN PATENT DOCUMENTS

| | | |
|---|---|---|
| JP | 51-112379 | 10/1976 |
| JP | 56-89036 | 7/1981 |
| JP | 61-104347 | 7/1986 |
| JP | 1-165405 | 11/1989 |
| JP | 02-132302 | 5/1990 |
| JP | 5-5397 | 1/1993 |
| JP | 5-296709 | 11/1993 |
| JP | 6-102980 | 4/1994 |
| JP | 7-128166 | 5/1995 |
| JP | 8-62061 | 3/1996 |
| JP | 08-327309 | 12/1996 |
| JP | 9-26367 | 1/1997 |
| JP | 10-141910 | 5/1998 |
| JP | 2001-153811 | 6/2001 |
| JP | 2002-113685 | 4/2002 |
| JP | 2002-188902 | 7/2002 |
| JP | 2004-358634 | 12/2004 |
| JP | 2005-195342 | 7/2005 |
| WO | WO-00/66970 | 11/2000 |
| WO | WO-02/37466 A1 | 5/2002 |

* cited by examiner

<Back side of Hand>　　<Palm side of Hand>

CONVEXO CONCAVE AMPLIFYING DEVICE AND CONVEXO CONCAVE DETECTING METHOD BY USE THEREOF, DEFORMATION SENSING DEVICE AND CONVEXO CONCAVE DETECTING METHOD BY USE THEREOF, AND CONVEXO CONCAVE POSITION EXHIBITING DEVICE AND CONVEXO CONCAVE POSITION EXHIBITING METHOD

TECHNICAL FIELD

The present invention relates to convexo concave amplifying device and convexo concave detecting method using it, to be used for detecting a convexo concave of an object such as a surface of a steel plate. Also it relates to deformation sensing device and convexo concave detecting method using it, to be used as a sensor for detecting a property of the object such as the convexo concave and a stress acting thereonto.

Further, it relates to convexo concave position exhibiting device and convexo concave position exhibiting method for exhibiting a position where the convexo concave is detected.

BACKGROUND ART

In the following, a background art of convexo concave amplifying device and convexo concave detecting method using it, deformation sensing device and convexo concave detecting method using it, and convexo concave position exhibiting device and convexo concave position exhibiting method will be explained.

1. Convexo Concave Amplifying Device and Convexo Concave Detecting Method by Use Thereof In a field of a tactile substitution and an artificial reality, many studies have been made for exhibiting an artificial feeling for human. For example, a tactile sensing exhibiting system whose sensing portion and displaying portion are disposed on the two sides thereof has been developed. An optical sensor reading a printed matter and a touch sensor are disposed as the sensing portion. For the displaying portion, a method of exhibiting the artificial tactile sensing by electrically stimulating a tactile receptor is adapted. Thus, this tactile sensing exhibiting system can exhibit the feeling of touching the thing which the user can not feel by himself.

However, the resolution and the sensitivity of the sensing portion and the displaying portion are insufficient. Also, the tactile sensing exhibiting system using a complex mechatronics technique is apt to invite trouble due to the complex structure. Thus, much time and labor are required for the maintenance. Further, sensing portion and the display portion can hardly be downsized.

U.S. Pat. Nos. 4,657,021 and 4,793,354 disclose means for easily detecting or sensing the convexo concave of the object. The detecting means is a touch enhancing pad comprised of two flexible sheets, and small amount of lubricant oil sealed between the two sheets. In using the touch enhancing pad, with one sheet being contacted and rested on a surface of a subject, the other sheet in contact with the finger is moved together with the finger.

As a result, movement of the lubricant oil reduces influence of friction between the subject and the fingertip, whereby the convexo concave of object can be clearly detected by smooth moving of the finger-tip. This touch enhancing pad has been put into the market by the name of "BSE (Breast Self-Examination) Pad", and is approved by FDA as a self-examination assisting tool for the breast cancer.

Generally, the tactile sensing of the finger may get dull on the condition that some intervening material is interposed between the surface of the object and the finger tip. This pad can, without using the complex mechatronics technique, detect the object convexo concave clearly. However, it can hardly detect the small or fine convexo concave, and is not practical as the tool to detect the convexo concave of the object extensively. Further, though it has a simple construction that the lubricant oil is sealed between the two sheets, it is afraided that the lubricant oil is leaked by the damage of the sheet.

The technique for detecting the convexo concave of the object has been required in many field. In the convexo concave detecting method, the subject (surface of the object) has been inspected by contacting for example a dialogue type sensor (contact type), or by an image processing (non-contact type). However, the former type is not suitable for the extensive inspection of the object. The latter type suffers from dispersion of the detected result due to luster and blot existed on the surface of the object. Further, the both types requires expensive apparatus and much time for setting.

Therefore, in the strain inspection of a steel plate of manufacturing process in practice, for example, vehicle manufacturing process, skilled workers detect the convexo concave by the hand. However, difference in degree of skill brings different result of the detection. In addition, long period is required for the workers to acquire the skill of detecting the convexo concave. For this reason, the detecting method which can be carried out cheaply and which can detect the convexo concave easily has been required.

2. Deformation Sensing Device and Convexo Concave Detecting Method by Use Thereof In these days, there have been many social problems such as extremely small birth rate, aging and medical care. The numbers of persons supporting a welfare service and an infrastructure may become short in the future. For this reason, a human-type robot (humanoid) which moves and reacts in the same way as the human may be required in the society. In order not to harm the person, the human-type robot needs to be covered by an artificial skin made of a soft material. Also, the artificial skin needs to have a tactile sensing function equivalent to the human skin, for example the functions to sense contact with the object and property of the object.

For realizing such function, the artificial skin in which a strain sensing elements such as a strain gauge or PVDF (polyvinylidene fluoride) sensor is embedded into the flexible material such a rubber etc. have been developed and used. However, due to poor or small elasticity and flexibility, the strain sensing element disposed in the flexible material may be broken by the stress concentration thereof. The strain sensing element and the flexible material may be peeled, or the flexible material may be cracked. In addition, since the strain gauge or the PVDF sensor has the limit of detection range, it is difficult to use them combined with the flexible material.

A tactile sensing sheet using a pressure sensitive rubber which can sense the stress acting in the normal direction thereof has been known. It however can not sense the stress acting in the tangential direction (shearing stress)

For example, Japanese unexamined patent publication H05-5397 has disclosed an external force measuring apparatus of shield excavator comprising a load detecting portion and a pressure receiving plate. One end of the load detecting portion is fixed to a bottom plate of a concave portion, and a strain gauge is mounted on the load detecting portion. The pressure receiving plate is fixed to the other end of the load detecting portion.

In this external force measuring apparatus, the external force received by the pressure receiving plate is transmitted to the strain gauge of the load detecting portion to be measured. However, if the both ends of the load detecting portion are fixed, there is a possibility that the strain gauge is broken by that the load detecting portion distorts largely. For this reason, applying the construction of H05-5397 to the flexible material can not overcome the breakage of strain gauge. Larger strain of the load detecting portion may surpass the detection range of the strain gauge.

3. Convexo Concave Position Exhibiting Device and Convexo Concave Position Exhibiting Method As mentioned above, in the manufacturing process in practice, the skilled worker detects the convexo concave on the surface. The method of easily detecting the convexo concave and easily finding out the position of the convexo concave has been required.

With regard to exhibiting the result from detecting the surface information of the object by several sensors, for example, an invisible convexo concave on the surface of the steel plate, it is general to display the image-processed result from sensing the surface information by a detecting member (c.f. Japanese unexamined patent publication 2001-153811).

However, in order to exhibit the detected position by displaying the surface information detected by the detecting member, the position where the detecting member is detecting is needed to be measured by using a magnetic sensor, a passive linkage system, a CCD camera, and so on. Therefore, the detecting apparatus becomes large, requires a large installation space, and has a difficulty in transporting.

Instead of displaying, sounding may be used for exhibiting that the sensor detects the information on the predetermined condition. However, it is difficult to find out the detected position at the moment of sounding in the case that the surface of the object is extensively sensed with time.

DISCLOSURE OF THE INVENTION

1. Convexo Concave Amplifying Device and Convexo Concave Detecting Method by Use Thereof By taking the above circumstances into consideration, the present invention intends to provide the convexo concave amplifying device which has a simple construction and can exhibit a convexo concave by amplifying a sense of a convexo concave of the object. It also provides a convexo concave detecting method which detects the convexo concave of the object by using the convexo concave amplifying device.

A convexo concave amplifying device for exhibiting a convexo concave by amplifying a sense of a convexo concave of an object of the present invention comprises a sensing member comprising a flexible sheet able to contact with the surface of the object and to deform along the surface of the object; and an exhibiting member that is formed on a surface of the flexible sheet and has a deformation resistance smaller than that of the flexible sheet in at least one of directions orthogonal to a direction of thickness of the flexible sheet.

According to this construction, the convexo concave amplifying device is able to exhibit the convexo concave by that the exhibiting member exactly amplifies the sense of the convexo concave of the object, which is sensed by the sheet member. Without the use of a complex mechatronics technique, the convexo concave amplifying device has a simple configuration comprising the sensing member and exhibiting member so that breakdown or breakage hardly happens and the cost is low.

The exhibiting member preferably comprises plural protrusions spaced each other and formed on the surface of flexible sheet. According to this construction, the exhibiting member is able to exhibit the convexo concave by effectively amplifying the sense of the convexo concave. The protrusions are preferably plates arranged in parallel, or are columns arranged by the predetermined interval. The protrusions preferably have a deformation resistance smaller than that of the flexible sheet in a direction orthogonal to the direction of thickness of the flexible sheet.

A convexo concave detecting method for detecting a convexo concave of an object of the present invention comprises a process of using a convexo concave amplifying device comprising a sensing member comprising a flexible sheet and an exhibiting member that is formed on a surface of the flexible sheet and has a deformation resistance smaller than that of the flexible sheet in at least one of directions orthogonal to a direction of thickness of the flexible sheet.

The process comprises a contacting step of contacting the sensing member with a surface of the object and deforming the flexible sheet of the sensing member along the surface of the object, and a detecting step of detecting the convexo concave by sensing a deformation of the exhibiting member induced in the contacting step.

According to this convexo concave detecting method, the convexo concave can be easily detected by amplifying the sense of the convexo concave through the contacting step and the detecting step. Since the deformation of the exhibiting member is detected on the condition that the detecting member is deformed along the surface of the object, the amplified information of the convexo concave can be exactly exhibited.

In the process of the convexo concave detecting method, the contacting step may be the step of pressing the flexible sheet onto and the surface of the object and deforming the flexible sheet along the surface of the object comprising a surface portion having flexibility and a convexo concave portion having a convexo concave covered by the surface portion. And the detecting step may be the step of detecting the convexo concave of the convexo concave portion. The convexo concave of the object comprising a surface portion having flexibility and a convexo concave portion having a convexo concave covered by the surface portion as well as the object having a convexo concave on the surface thereof can be detected by pressing the flexible sheet onto and the surface of the object and deforming the flexible sheet along the surface of the object in the contacting step.

The convexo concave amplifying device in contact with the surface of the object is preferably slid in the contacting step, thereby an amount of the deformation of the exhibiting member is induced to depend on time, and a variation of a time-dependent amount of the deformation of the exhibiting member is preferably sensed by a tactile sensing in the detecting step. According to above process, since the deformation of the exhibiting member can be detected by tactile sense, the inspector can sharply recognize the convexo concave.

2. Deformation Sensing Device and Convexo Concave Detecting Method by Use Thereof By taking the above background art circumstances into consideration, the present invention intends to provide the deformation sensing device having a simple structure and a break-proof structure for large deformation. It also provides a convexo concave detecting method which detects the convexo concave of the object by using the deformation sensing device.

A deformation sensing device for sensing a deformation thereof of the present invention, comprises a capsule deformable by stress, a viscous fluid contained in the capsule, and a relative movement sensing member that is disposed inside of the capsule and senses a relative movement against the viscous fluid.

The relative movement sensing member is preferably protruded inside from an inner face of the capsule. Since the relative movement sensing member senses relative movement between the capsule and the viscous fluid occurred in accordance with the capsule deformation, deformation of the capsule is not directly transmitted to the relative movement sensing member. Since the relative movement sensing member is difficult to deform even though the capsule is largely deformed, the relative movement sensing member is difficult to be broken.

The deformation sensing device of the present invention can sense, in addition to the stress acting in the normal direction, the stress acting in the tangential direction. The property such as convexo concave and the texture can be sensed. The relative movement sensing member preferably comprises a strain sensing tool, and the strain sensing tool is preferably a strain gauge or a PVDF sensor. The relative movement sensing member preferably comprises a plate strained by a movement of the viscous fluid, and the strain sensing tool is preferably disposed on the plate.

Since the relative movement sensing member is difficult to largely deform, the strain sensing tool can be prevented from breaking down even if the strain sensing tool is disposed on the plate.

A convexo concave detecting method for detecting a convexo concave of an object of the present invention, comprises a process of using a deformation sensing device comprising a capsule containing a viscous fluid therein and deformable by stress, and a relative movement sensing member that is disposed inside of the capsule and senses a relative movement against the viscous fluid, wherein the process comprises a step that the deformation sensing device and the object are moved relatively on a condition that the deformation sensing device is in contact with a surface of the object.

According to the convexo concave detecting method using the deformation sensing device, the deformation sensing device can be deformed at the position where a convexo concave exists on the surface of an object by the way how the deformation sensing device in contact with the surface of the object is slid and the deformation sensing device and the object are relatively moved. Thus, the deformation sensing device detects the deformation of the capsule and the convexo concave.

3. Convexo Concave Position Exhibiting Device and Convexo Concave Position Exhibiting Method By taking the above background art circumstances into consideration, the present invention intends to provided the convexo concave position exhibiting device which has a simple structure and can exhibit the position where the convexo concave is sensed, and convexo concave position exhibiting method by using it.

A convexo concave position exhibiting device of the present invention comprises a sensing-and-exhibiting member and a controlling member. The sensing-and-exhibiting member comprises a sensing portion comprising plural deformation sensing devices of sensing a deformation thereof caused by a convexo concave of an object, and an exhibiting portion comprising plural light emitters and located opposite to the sensing portion. The controlling member of controlling the light emitters emits light depending on a result of sensing by the deformation sensing devices.

According to the convexo concave position exhibiting device of the preset invention, the position of an invisible convexo concave can be easily recognized on the surface of the object by light-emission of the light emitter. It has the simple structure comprising the sensing-and-exhibiting member and the controlling member. Since the exhibiting portion is located opposite to the sensing portion, the position of the deformation sensing device need not be measured.

The sensing-and-exhibiting member has a shape of a bag able to be worn by a hand, wherein the sensing portion is operable on a palm side of the hand, and the exhibiting portion is operable on a back side of the hand. The bag-shaped sensing-and-exhibiting member is suitable for wearing by hand, easy operation, and easy carrying.

A convexo concave position exhibiting method for exhibiting a position of a convexo concave of an object of the present invention, comprises a relative moving step that a deformation sensing device and the object are moved relatively on a condition that the deformation sensing device is in contact with a surface of the object, a detecting step of detecting the convexo concave by that the deformation sensing device senses a deformation thereof caused by a convexo concave of the object, and an exhibiting step of time-dependently exhibiting a position of the convexo concave by emitting light depending on a result of detecting in the detecting step.

According to the convexo concave position exhibiting method of the present invention, the position of an invisible convexo concave can be easily recognized on the surface of the object by light-emission of the light emitter. Since the position of the convexo concave is time-dependently exhibited by emitting light depending on the result of detecting in the detecting step, relative movement between the deformation sensing device and the object in the relative moving step enables the extensive detection.

The deformation sensing device in contact with the surface of the object is preferably slid in the relative moving step. Even if the convexo concave position exhibiting device is slid on the surface of the object in high speed, the plural light emitters can emit the light one after another at the position where the deformation is sensed. Since the position where the convexo concave is sensed remains on the retina as the residual image of light, the position can be exactly recognized on the surface of the object.

The exhibiting step is preferably a step of exhibiting the position of the convexo concave on the surface of the object by emitting light at the position where the convexo concave exists. The position of the convexo concave is exactly recognized by the way of emitting at the position where the convexo concave exists.

BEST MODE FOR CARRYING OUT THE INVENTION

Figure 1:
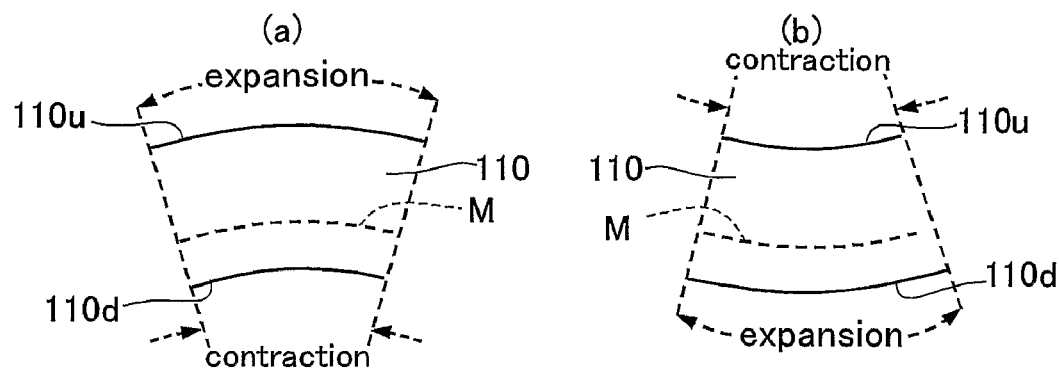
FIG. 1(a) schematically shows elasticity (expansion and contraction) occurred when the conventional sheet contact with the convex surface of an object, 1(b) shows elasticity occurred when the conventional sheet contact with the concave of the object.

In the following, best modes of a convexo concave amplifying device and a convexo concave detecting method of the present invention, will be explained with FIGS. 1 to 3. Also, best mode of a deformation sensing device and a convexo concave detecting method using the deformation sensing device of the present invention, will be explained with FIGS. 4 to 9.

Figure 10:
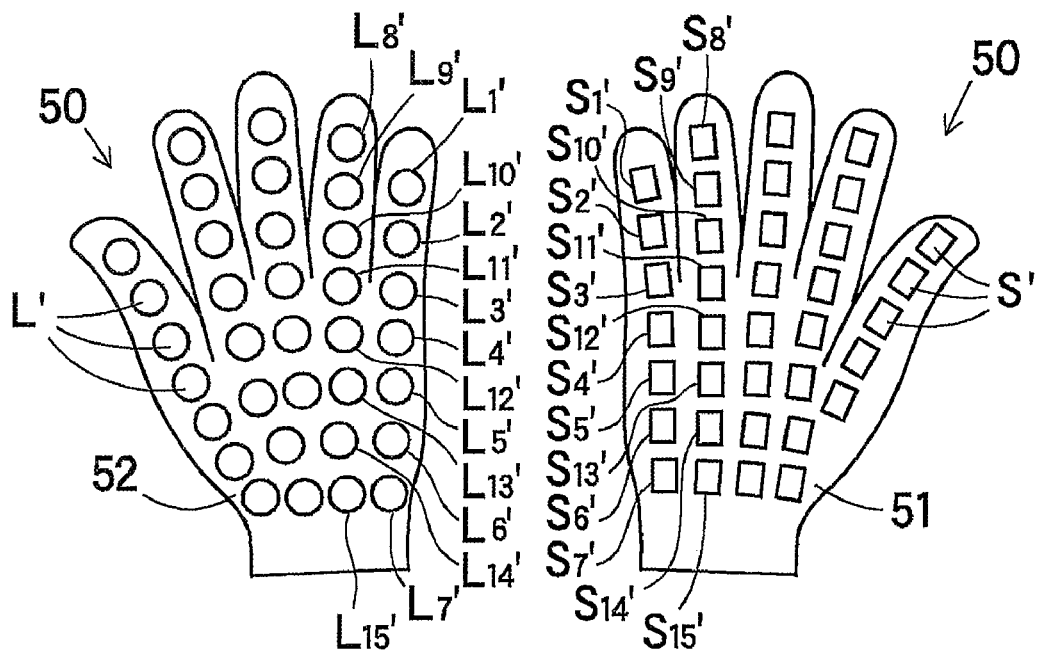
FIG. 10 are the plane views showing one example of the convexo concave position exhibiting device of the present invention when it is viewed from the back side of hand (left figure) and from the palm side of hand (right figure)
Figure 11:
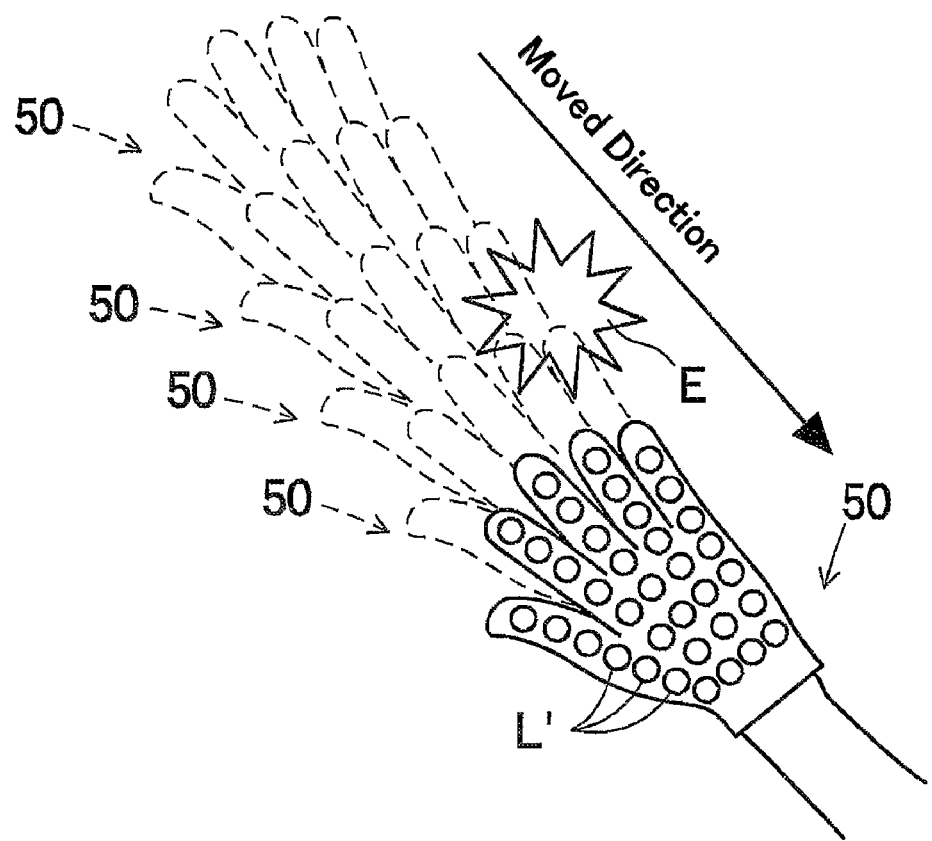
FIG. 11 is an explanatory view showing the convexo concave position exhibiting method by the convexo concave position exhibiting device.

Further, best mode of a convexo concave position exhibiting device and a convexo concave position exhibiting method of the present invention will be explained with FIGS. 10 and 11.

1. Convexo Concave Amplifying Device and Convexo Concave Detecting Method by Use Thereof A convexo concave amplifying device of the present invention senses a convexo concave of an object to exhibit it with amplification. When a sheet having a constant composition and a constant thickness is contacted with a surface of an object at one surface (a lower surface, for example), the sheet deforms or deflects along the convexo concave of the object. In the deflection, expansion and contraction occur in an upper and a lower surfaces of the sheet. Concretely, as shown in FIG. 1 schematically, when the sheet 110 is mechanically adapted to (contacted with) the convex surface of the object, expansion occurs in the upper surface 110$u$ while contraction occurs in the lower surface 110$d$ (refer to FIG. 1($a$)). When the sheet 110 is mechanically contacted with the concave surface, reversed phenomenon occurs (refer to FIG. (1$b$)).

In both cases, an intermediate or neutral surface M not expanding and contracting exists in the sheet 110. As the upper surface of the sheet goes away from the intermediate surface M, that is as thickness of the sheet becomes larger, expansion/contraction amount of the sheet upper surface becomes larger. Thus, for exhibiting the convexo concave detected on the upper surface with amplification, thickness of the sheet is desirably increased to make deformed amount of the sheet upper surface larger.

However, in the general sheet which is isotropic and has constant thickness, flexibility is lowered when the sheet thickness is increased (bending rigidity is proportional to cube of thickness). For this reason, the thicker sheet which is hardly mechanically contacted with the object surface (surface of the object) at the lower surface thereof, can not sense the object convexo concave (the convexo concave of the object) accurately. If the sheet of lower elastic modulus is used, it is compressed in the thickness direction by pressing force applied. Thus, the convexo concave detected by the lower surface is hardly transmitted to the upper surface.

In view of the above, the convexo concave amplifying device of the present invention is comprised of a sensing member, and an exhibiting member. The sensing member is comprising a flexible sheet to be able to contact with the surface of the object and to deform along the surface of the object. The exhibiting member is formed on a surface of the flexible sheet. Deformation resistance of the exhibiting member is smaller than that of the flexible sheet in at least one of directions orthogonal to a direction of thickness (extended or spread direction) of the flexible sheet.

When the sensing member constructing the convexo concave amplifying device is mechanically contacted with the object at one surface (hereinafter, briefly called "lower surface of the sensing member"), it deforms following to the object surface due to flexibility thereof. The exhibiting member on the other surface of the sensing member (hereinafter briefly called "upper surface of the sensing member") also deforms.

Deformation resistance of the exhibiting member in at least one direction in the spread direction is smaller than that of the sensing member in the same direction. Thus, the flexibility of the sensing member is not degraded even if the thickness of the convexo concave amplifying device is large as a whole. As a result, the exhibiting member can effectively exhibit the object convexo concave sensed with amplification. In the following, the principle will be explained concretely.

Figure 2:
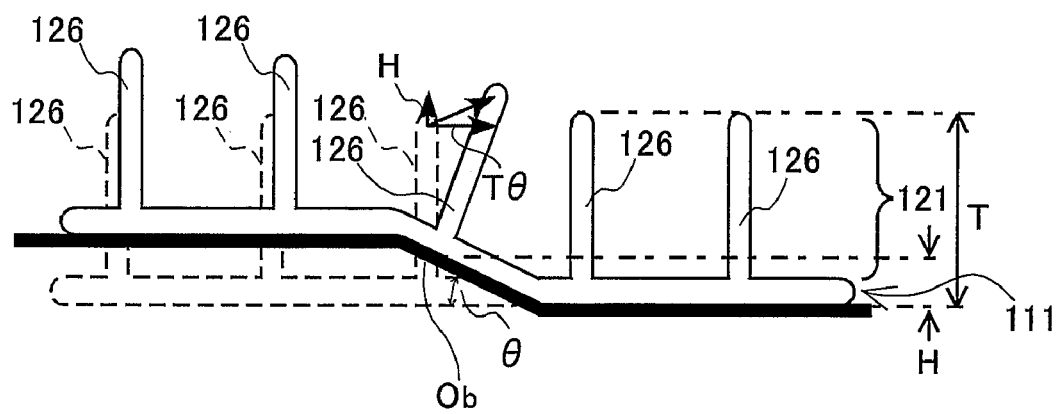
FIG. 2 schematically shows deformation of the sensing member and the exhibiting member when the convexo concave amplifying device of the present invention is contact with the flat surface (shown by the dotted line) and the inclined surface (shown by the solid line)
Figure 3:
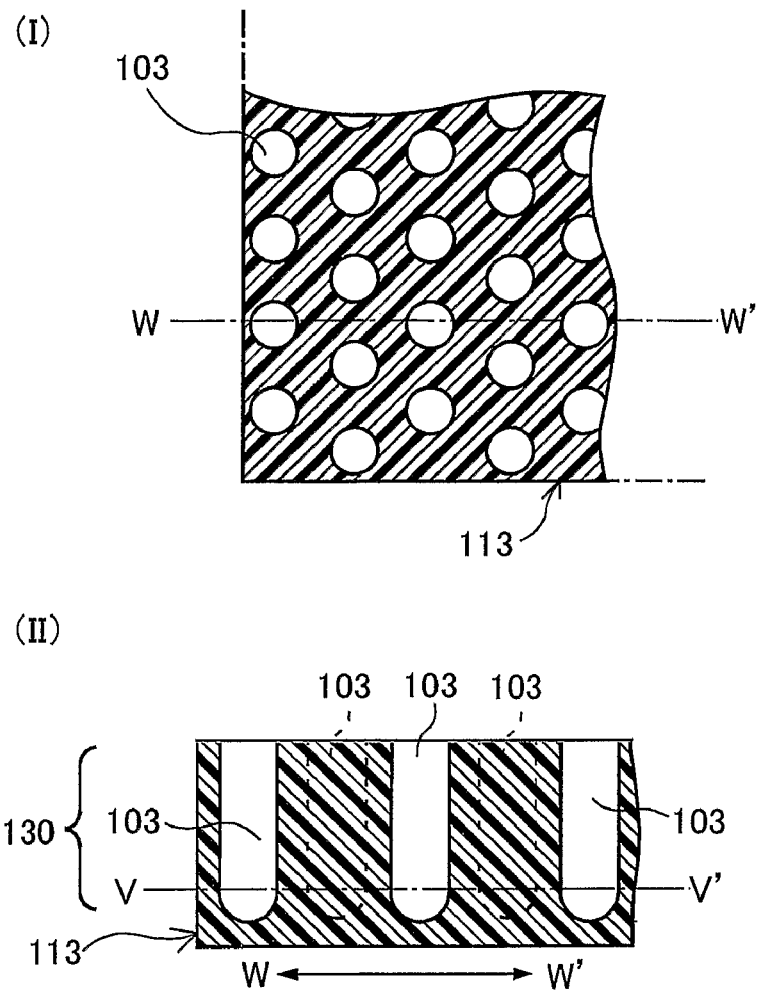
FIG. 3(I) is an enlarged cross-sectional view along a line V-V' in FIG. 3(II), and FIG. 3(II) is an enlarged cross-sectional view along a line W-W' in FIG. 3(I)

In FIG. 2, a convexo concave amplifying device is shown schematically in the two-dimensional space. It is comprised of a sensing member 111, and an exhibiting member 121 formed on the sensing member 111. A deformation resistance of the exhibiting member 121 in the spread direction of the sensing member 111 is small. The exhibiting member 121 includes plural pin-like protrusions 126 extending in the thickness direction (up-down direction in FIG. 2), and separated equidistantly in the spread direction (lateral direction in FIG. 2). Namely, the deformation resistance of the exhibiting member 121 in the lateral direction is smaller than that of the sensing member 111 in the same direction.

In FIG. 2, the convexo concave amplifying device put on a flat (standard) surface is shown by a dotted line, while that put on an inclined surface (inclined angle: θ) is shown by a solid line. When the convexo concave amplifying device is put on the inclined surface, the protrusions 126 of the exhibiting member 121 deform or incline in a normal direction and a tangential direction of the standard surface.

Provided that the neutral surface M exists in the sensing member 111 and thickness of the sensing member 111 is extremely small, deformation or inclination of the protrusions 126 in the tangential direction is proportional to product of the inclined angle θ of the inclined surface Ob, and thickness T of the convexo concave amplifying device. Here, thickness T is sum of thickness of the sensing member 111 and length of the protrusions 126. Inclination of the protrusions 126 in the normal direction is equal to height H of the inclined surface Ob.

Summing up, thanks to the convexo concave amplifying device of the present invention comprised of the sensing member and the exhibiting member, the thicker or longer exhibiting member can amplify and to exhibit the object convexo concave sensed by the sensing member accurately.

In the convexo concave amplifying device, deformation resistance of the exhibiting member in at least one direction in the spread direction is smaller than that of the sensing member in the same direction. The intermediate surface M at which no expansion or contraction occurs, positions remote from the surface of exhibiting member. For this reason, the object convexo concave sensed by the sensing member can be effectively amplified by the exhibiting member to be exhibited on the surface thereof.

Further, thanks to the above structure, even if thickness or length from the intermediate surface M to the exhibiting member surface is selected larger, flexibility of sensing member does not decrease, and the amplifying effect of the exhibiting member increases.

By selecting thickness of the sensing member smaller and length of the exhibiting member larger, the convexo concave amplifying device convenient to effectively senses the object convexo concave, amplifies and exhibits the sensed convexo concave can be obtained. For example, ratio between thickness of the sensing member and length of the exhibiting member can range from 1:10 to 1:100.

(i) Sensing Member

In the convexo concave amplifying device of the present invention, the sensing member has flexibility to deform following (tracing) along the object surface. This is because the lower surface of the sensing member is contacted (touched) with the object surface, or it is pressed onto the object surface. Preferable elastic modulus of sensing member ranges from 500 to 3000 MPa, 1500 to 2500 MPa is more preferable. For realizing such elastic modulus, the sensing member can be made of resin such as polyethyleneterephthalate (PET), polyacetal or polycarbonate. Preferable thickness of the sensing member ranges from 0.05 to 0.5 mm, depending on the elastic modulus.

The convexo concave amplifying device in which the elastic modulus and thickness of the sensing member are selected in the above ranges, can easily deforms following to the object surface at one surface thereof. Thus, the convexo concave amplifying device is effectively used to sense the convexo concave of object. Thanks to small expansion and contraction of the sensing member in the thickness direction, the sensing member can hold the spatial information of the object convexo concave to transmit as the information in the thickness direction.

When selecting material of the sensing member, the friction between the lower surface of it and the object surface is preferably considered. Small friction is preferable to obtain smooth and easy sliding of the convexo concave amplifying device on the object surface (to be explained later). If the material of sensing member increases the friction, another member which can reduce the friction but does not decrease flexibility of the sensing member, can be added on the lower surface of the sensing member. For such added member, a film or a tape made of material different from the material of sensing member can be adopted.

(ii) Exhibiting Member

The exhibiting member of the convexo concave amplifying device of the present invention is formed other surface (for example upper surface) opposite to one surface (for example lower surface) of the sensing member contacting with the object. It can be formed integrally with the sensing member.

The exhibiting member has a deformation resistance smaller than that of the flexible sheet in at least one of directions orthogonal to a direction of thickness of the flexible sheet. Material and shape of the exhibiting member not reducing flexibility of the sensing member are preferably selected. The exhibiting member has a rigidity not generating expansion and contraction, when surface of the exhibiting member is compressed in the thickness direction of the convexo concave amplifying device.

As the material of the exhibiting member, an anisotropy material of which the deformation resistance differs depending on the deforming direction is preferably adopted. A reinforced fiber plastic and a high function resin can be exemplified. In addition to the single layer construction of the exhibiting member (the convexo concave amplifying device has the double construction of the sensing member and the exhibiting member), the exhibiting member can have plural-layer construction. In such exhibiting member, plural layers having the deformation resistance of which direction and value are different from that of the sensing member can be adopted. Also, the direction and value of the deforming resistance can be gradually varied from the one surface to the other surface. In such case, selecting the deformation resistance at the front surface of the exhibiting member smaller is preferable.

The exhibiting member can be made of foam, and a sheet provided with plural holes. In the convexo concave amplifying device schematically shown in FIG. 3, the exhibiting member is constructed by the sheet having plural holes extending in a direction of the thickness thereof. The convexo concave amplifying device is comprised of a sensing member 113, and a exhibiting member 130 constructed by the sheet. They are integrally constructed by resin material. The exhibiting member 130 is provided with plural vertical dead ended holes 103 extending vertically from the upper surface thereof.

The vertical holes 103 make the deformation resistance of the exhibiting member 130 in the spread direction of sensing member smaller than that of the sensing member 113 in the same direction. The sensing member 113 and the exhibiting member 130 separately formed can be fixed integral each other. The holes can be formed in a direction to make a predetermined angle relative to the thickness direction of the sensing member.

The exhibiting member is preferably comprised plural protrusions spaced each other and formed on the surface of the flexible sheet. The exhibiting member preferably has rigidity not to be expanded or contracted in the length direction thereof even when tip ends of the protrusions (surface of the exhibiting member) are pressed, and to maintain the angle of the protrusions relative to the sensing member constant. With inclination of the protrusions by the predetermined angle, the tip ends of the protrusions displace or shift by the predetermined amount, to thereby amplify and to exhibit the object convexo concave detected by the sensing member.

The preferable elastic modulus of the protrusions ranges from 1500 to 5000 MPa, and 2000 to 4000 MPa is more preferable. For realizing such value of elastic modulus, the protrusions can be made of resin such as PET, polyacetal, polycarbonate and acryl etc., and metal such as aluminum etc. The protrusions having such range of the elastic modulus does not degrade the flexibility of the sensing member.

There is no restriction for shape of the protrusions. A cone shape and pyramid shape, a column shape and cylinder shape, and plate shape and napping shape can exhibit the convexo concave amplifying effect. The tip end of the protrusion can have a sharp shape, flat shape and curved shape. When the protrusion has the cone shape or the column shape, a hemisphere tip end is preferable.

There is no restriction for arrangement of the protrusions. They can be arranged at random, but arranging the protrusion by the predetermined interval in the two-dimensional space is preferable. In view of shape and size of the protrusions, the interval of 0.5 to 2.0 mm is preferable. The protrusions can position at cross points of grids, and can be arranged in parallel to each other, or to cross with each other. For example, in the protrusions constructed by the plural plates arranged in parallel each other, the deformation resistance in the spread direction of the sensing member, and orthogonal to the arranged direction of the protrusions can be made smaller.

The protrusions constructed by the plural columns arranged by the predetermined interval can decrease the deformation resistance in the spread direction of the sensing member.

The plural protrusions are preferably arranged so that the tip ends thereof are directed in parallel. In such arrangement, all of the protrusions displace by the same amount relative to the object convexo concave, to amplify the convexo concave. For example, when the plural protrusions are constructed by the columns extending in the thickness direction of the sensing member, the expansion or contraction hardly occurs even if the tip ends thereof are compressed, whereby the convexo concave amplifying device is contacted with the object. Also, such protrusions easily hold vertical posture so that the exhibiting member surface (tip end of the plural protrusions) can accurately amplify and exhibit the object convexo concave.

As thickness of the convexo concave amplifying device becomes larger, that is as the protrusions become longer, the amplifying effect increases. For this reason, length of the protrusion can preferably selected longer, so long as no expansion or contraction occurs during usage. In view of the shape and material, the preferable length of the protrusion is not less than 2.5 mm. The length of 3 to 6 mm is more preferable. The column-shaped and cone-shaped protrusions preferably has diameter of 1 to 1.5 mm at a connecting part between the protrusion and the sensing member. The protrusions having such diameter do not reduce flexibility of the sensing member.

Selecting the material and thickness of the sensing member and the exhibiting member, and selecting the shape of the exhibiting member, can vary amount of the deformation resistance and deformed degree of the exhibiting member. Thus, value of the flexibility of the sensing member and the amplifying operation of the convexo concave amplifying device can be varied. The material, thickness and shape can be selected in view of the quality (resolution of convexo concave) and usage. Also filling in the hollow space of the hole (for example, vertical hole 103 of FIG. 3) and space formed between the adjacent protrusions of the exhibiting member with various filling material can adjust the deformation resistance of the exhibiting member.

The sensing member and the exhibiting member independently prepared can be joined, or the sensing member and the exhibiting member can be made integral by one body of the same material. In the latter case, preferable elastic modulus is 1500 to 3000 MPa, and 2400 to 2500 MPa is more preferable. For the manufacturing of the sensing member and exhibiting member, various forming method using the molds and stereolithography can be adopted.

The exhibiting member preferably has a strain sensing tool for detecting strain thereof. For example, a strain gauge can be exemplified. The strain gauge of an electrical resistance type can convert the physical deformation of the exhibiting member to the electrical signal. The strain sensing tool sensing deformation of the exhibiting member surface can sense the object convexo concave in the higher accuracy, because the convexo concave of the object is amplified by the exhibiting member surface. The strain sensing tool can be disposed at any position where it can sense deformation of the exhibiting member.

(iii) Convexo Concave Detecting Method

Next, convexo concave detecting method by the convexo concave amplifying device of the present invention will be explained.

This convexo concave detecting method is comprised of a contacting step, and a detecting step. In the contacting step, the sensing member is contacted with a surface of the object and deformed the flexible sheet of the sensing member along the surface of the object. In the detecting step, the convexo concave is detected by sensing a deformation of the exhibiting member induced in the contacting step.

As partially explained in the above, the exhibiting member formed on the sensing member deforms following to the object convexo concave sensed by the sensing member. The exhibiting member deforms corresponding to surface shape of the object (flat or inclined, refer to FIG. 2). Sensing deformation of the exhibiting member on the condition the sensing member is contacted with the object convexo concave can detect object convexo concave.

The convexo concave detecting method can also detect convexo concave within the object comprised of a convexo concave portion, and a surface portion covering it. In the contacting step, the sensing member of the convexo concave amplifying device is pressed onto object and is deformed along the surface of the object. The convexo concave amplifying device can, in the detecting step, detects the convexo concave of the convexo concave portion. Thus, the convexo concave detecting method can detect a small foreign matter entered below the flexible thing such as the sheet, and lump in the skin.

There is no restriction for the sensing deformation of the exhibiting member. However, in the contacting step, the convexo concave amplifying device contacted with the surface of the object is slid, thereby an amount of the deformation of the exhibiting member is induced to depend on time. In the detecting step, a variation of a time-dependent amount of the deformation of the exhibiting member is sensed by a tactile sense. Hereinafter, sensing method by the tactile will be explained.

A human skin having the tactile is comprised of three layers of different softness. They are arranged in the order of a epidermis (surface skin), dermis and hypodermic tissue from outside. Inside of the human skin where no hair is grown, there are four feeling receptive organs (Meissner's corpuscle, Merkel disk receptor, Pacinian corpuscle and Ruffini ending). They convert the strain information of the skin tissue to the electrical pulse, then the electrical pulse is transmitted to a central nervous system to generate the skin feeling.

These feeling receptive organs are positioned at different depth from the surface skin, and are characterized by size of receptive field (area on the skin surface where receptive organs receive the stimulus) and speed to adaptation. Among the four feeling receptive organs, Meissner's corpuscle positioned at boundary between the epidermis and the dermis, has high spatial resolution due to narrow receptive field, and has quick adaptation. It contributes, when a palm of hand or a finger is contacted with the object surface to follow it, to separate the feeling stimulus resulted from the object convexo concave. Thus, the position and shape of the convexo concave are sensed. When the convexo concave amplifying device is used to detect the object convexo concave, amplifying the stimulus reached to Meissner's corpuscle is effective.

The Meissner's corpuscle, in recognizing the object convexo concave, generates the electrical pulse corresponding to strain variation relative to lapse of time, not corresponding to the absolute amount of strain. Through structural analysis of Meissner's corpuscle, the time dependent strain variation in the shearing direction is suitable stimulus for the Meissner's corpuscle, has been well-known.

In the contacting step, the convexo concave amplifying device is compressed onto the object surface by the skin such as the palm of hand having the tactile sensing to be mechanically contacted thereto. The convexo concave amplifying device is slid together with the hand on the object surface so that displacement in the tangential and normal directions of the exhibiting member surface varies as the time passes. In the detecting step, time dependent displacement variation in the tangential direction acted onto the skin is transmitted to Meissner corpuscle in the skin, as the strain variation in the shearing direction which is suitable stimulus for the Meissner's corpuscle.

As partially explained, because the tangential displacement or inclination on the exhibiting member surface is proportional to inclination of the object surface and thickness of the convexo concave amplifying device, it is transmitted to the Meissner's corpuscle after being amplified by length of the exhibiting member. For this reason, when the object convexo concave is detected by the tactile sense, sliding the convexo concave amplifying device contacted with the object convexo concave by the hand is preferable.

When the exhibiting member of the convexo concave amplifying device is constructed by the protrusions, the time dependent strain variation in the shearing direction easily generates in the skin. Such strain variation is resulted from displacement variation of the tip ends of protrusions in the tangential direction. This is because the tangential displacement dispersedly applied at the tip ends of the protrusions to the skin easily generates the shearing strain. The tangential displacement is determined corresponding to height of the object convexo concave. The information of time dependent displacement variation is converted to the strain variation of the Meissner's corpuscle in the shearing direction.

For the above reason, according to the convexo concave detecting method, shape (inclination and height) of the object can be amplified and converted to strain variation in the shearing direction effectively at the position of Meissner's corpuscle by displacement variation of the exhibiting member surface of the convexo concave amplifying device.

Further, according to the convexo concave detecting method, the palm of hand etc. is slid, on the object surface via the convexo concave amplifying device having the sensing member of which lower surface is of the low friction. As a result, the friction between the sensing member and the object surface reduces to prevent a stick-slip vibration which may get dull the feeing. Reducing the friction which may become noise and the contacting stimulus resulted from vibration can make the sensation of the convexo concave clearer. The tip ends of the exhibiting member constructed by the plural protrusions contribute to prevent slippage between the convexo concave amplifying device and the skin.

The convexo concave detecting method using the detecting method by the tactile sensing, can be applied to a surface inspection of deformation existed on a surface of steel plate, in the vehicle manufacturing and ship-building. The surface inspection has been carried out conventionally by the skilled worker by moving the palm of hand along the steel plate surface. The convexo concave amplifying device used in the convexo concave detecting method is portable due to the simple construction thereof. In the working spot where a work globes are indispensable, the convexo concave amplifying device can be used by building it in the work glove. Thus, usage of the convexo concave amplifying device is enlarged.

The convexo concave amplifying device and the convexo concave detecting method can be utilized in a training of beginners who are working at the surface inspection. In the conventional training, the beginners should continue to trace the object surface until they detects the surface strain even when it seems flat for them. The convexo concave amplifying device and the convexo concave detecting method of the present invention capable of sensing the extremely small surface convexo-concave can acquire experience (scent) about position, size and shape of the surface convexo-concave easily.

The surface inspection using the acquired experiences enables sensing of the small convexo concave of the object without the convexo concave amplifying device. Thus, training effect of the tactile ability for the training workers is improved, so that the surface detecting skill can be succeeded via the convexo concave amplifying device of the present invention.

As partially explained, the convexo concave amplifying device can adjust the convexo concave amplifying degree thereof by changing of the material and thickness thereof, and construction of the exhibiting member. The beginner can increase the training efficiency by properly selecting various kinds of the convexo concave amplifying device according to the trained level. In the surface inspection of the vehicle manufacturing, the different kinds of convexo concave amplifying devices having different amplifying degree can be used for every kinds of the vehicle. Thus, the inspection level can be easily set corresponding to the kinds of vehicles.

Figure 4:
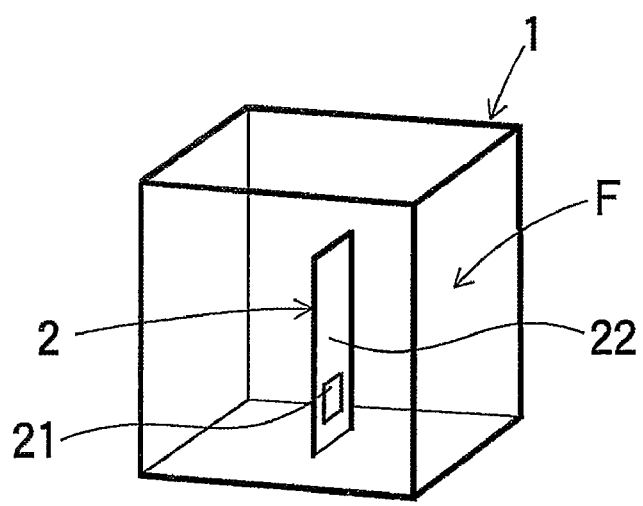
FIG. 4 is a perspective view, schematically showing one sample of the deformation sensing device of the present invention.
Figure 5:
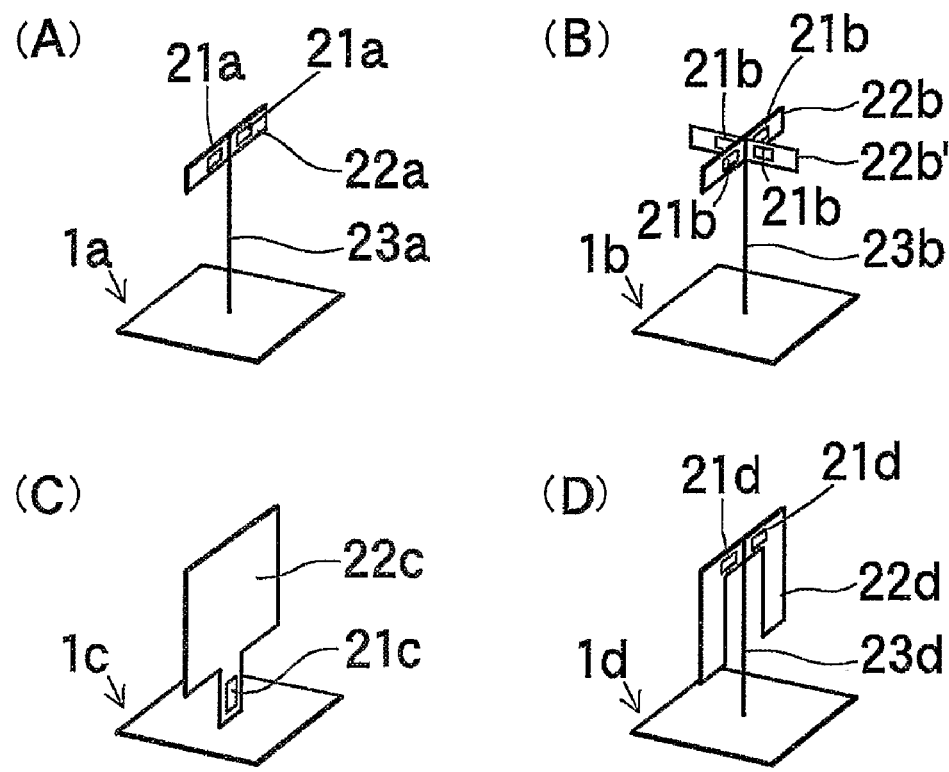
FIGS. 5(A) to (D) are perspective views showing concrete relative movement sensing member of the deformation sensing device.

2. Deformation Sensing Device and Convexo Concave Detecting Method by Use Thereof A deformation sensing device of the present invention is comprised of a capsule, a viscous fluid, and a relative movement sensing member. The capsule can deform by stress, and a viscous fluid is contained in the capsule. The relative movement sensing member is disposed inside of the capsule and senses a relative movement against the viscous fluid. FIG. 4 is a perspective view schematically showing one sample of the deformation sensing device. The deformation sensing device has a capsule 1 containing a viscous fluid F therein, and a relative movement sensing member 2 positioned on an inner surface of the capsule 1.

The capsule can be made of various material which can deform, when the stress is applied thereto, to be explained later. The capsule 1 shown in FIG. 4 has cubic shape, but other various shape which can hold the viscous fluid therein can be adopted. For example, polyhedron and sphere can be exemplified. Also, the capsule may be provided with a opening(s) at one part thereof.

The relative movement sensing member positioned on the inner surface of the capsule senses movement of the viscous fluid occurred when the capsule deforms. The relative movement sensing member senses movement of the viscous fluid flown corresponding to deformation of the capsule. Thus, deformation of the capsule is sensed by the relative movement sensing member. The relative movement sensing member senses deformation of the capsule even when it moves corresponding to deformation of the capsule, as long as there is relative movement between the relative movement sensing member and the viscous fluid.

The relative movement sensing member can have various structure to sense movement of the viscous fluid. The relative movement sensing member is preferably protruded inside from an inner face of the capsule, and is provided with a strain sensing tool such as a strain gauge or PVDF sensor. Using the relative movement sensing member having a plate to be flexed by movement of the viscous fluid can effectively senses movement of the viscous fluid. Here, the plate flexes by receiving movement of the viscous fluid as the viscous resistance when the capsule deforms. Even when the plate is moved by deformation of the capsule, it receives the viscous resistance from the viscous fluid.

The strain sensing tool is preferably attached to the plate, preferably to the position of the plate easily deformed. Concretely, as shown in FIG. 4, strip-like plate 22 is fixed at one end thereof to one wall portion of the capsule. The strain sensing tool is attached to a root portion of the plate 22. Another variations of the deformation sensing device are shown in FIGS. 5(A) to 5(D). In FIGS. 5(A), 5(B) and 5(D) rods 23a, 23b and 23d studded on the capsule wall and having high rigidity not flexed by movement of the viscous fluid, and plates 22a, 22b and 22d fixed to the rods are combined. In FIGS. 5(C) and 5(D), plates 22c and 22d studded on the capsule wall and having area receiving the viscous resistance are provided. Especially, the variation of FIG. 5(B) in which two plates 22b and 22b' are provided to cross each other, can sense deformation in various directions.

The plate can be constructed by an elastic member, and the elastic modulus can range from 1000 to 4000 MPa. It varies depending on amount of deformation to be sensed. Flexibility of the plate can be adjusted by adjusting the elastic modulus, size and length thereof. Thus, sensitivity of the deformation sensing device can be suitably selected. Selecting the most suitable flexibility of the plate corresponding to the detecting range of the strain sensing tool, enables the strain sensing tool to exhibit the maximum resolution.

In the embodying mode shown in FIG. 4, only one relative movement sensing member 2 is fixed to one wall portion of the capsule 1. However, plural relative movement sensing member can be fixed to one wall portion or plural wall portions. Plural relative movement sensing member can be fixed to the wall portion(s) so that the plates flexes in the same direction or in the different directions. In the latter case, deformation of the walls in plural directions can be sensed.

The viscous fluid flows corresponding to deformation of the capsule, of which movement is sensed by relative movement sensing member. Accordingly, it is enough that the viscous fluid is held to contact at least a part of the capsule and a part of the deformation sensing device. No serious problem arises even if any bubble or cavity is existed within the capsule. The viscous fluid is preferably a fluid of high viscosity such as a silicone oil of which viscosity variation relative to the temperature is small. The kinetic viscosity of the viscous fluid can range from $1 \times 10^4$ to $1 \times 10^7$ mm$^2$/sec, and varies deforming degree to be detected.

The capsule is made of various material having the flexibility and/or expansion-contraction property (elasticity). The capsule preferably has the elasticity to generate the deformation by the shearing stress, when detecting variation of the shearing stress acts onto the deformation sensing device. When detecting the force acting in the normal direction, the capsule preferably has the flexibility to deform in the normal direction. When detecting the object convexo concave, the capsule preferably has the flexibility to follow the object surface.

Operation of them will be explained below with reference to FIGS. 6 and 7. FIGS. 6(I) and 7(I) schematically show a cross-section of the deformation sensing device shown in FIG. 4. The relative movement sensing member 2 senses movement of the viscous fluid flowing in the left-right direction. Upper figure of FIG. 8 is a graph showing relation between deformation (shearing strain) occurred in the capsule 1 when the shearing stress acts onto the deformation sensing device and the lapse of time. Lower figure is a graph showing relation between the viscous resistance (resisting force) the relative movement sensing member 2 receives when the shearing stress acts onto the deformation sensing device and the lapse of time. The part (I), (II) and (III) in the both figures respectively correspond to FIGS. 6(I), 6(II) and 6(III), and FIGS. 7(I), 7(II) and 7(III). When the capsule 1 receives the shearing stress, the deformation sensing device firstly deforms to the state as shown in FIGS. 6(II) and 7(II), and then to the state as shown in FIGS. 6(III) and 7(III).

Figure 6:
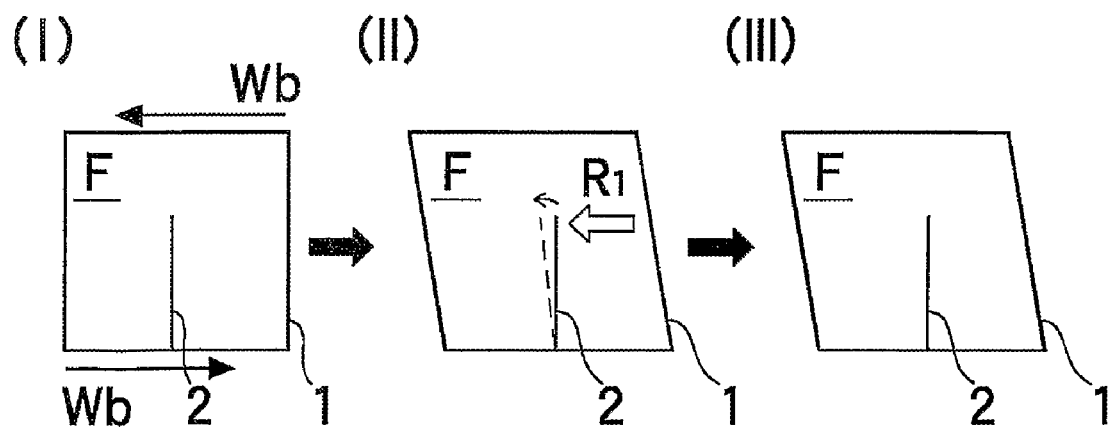
FIGS. 6(I) to (III) show deformation variation of the deformation sensing device receiving the shearing force in the Wb direction relative to the lapse of time.

As shown in FIG. 6(I), acting the shearing stress on the lower and upper surfaces of the deformation sensing device in the arrow direction Wb deforms the capsule 1 to the state shown in FIG. 6(II). The viscous fluid F flowing corresponding to deformation of the capsule 1 applies the viscous resistance in the arrow direction $R_1$ to the relative movement sensing member 2. The relative movement sensing member 2, receiving this viscous resistance, flexes as shown in FIG. 6(II) by the dotted line to detect movement of the viscous fluid F. Amount of the viscous resistance is gradually attenuated as the time passes (refer to FIG. 6(III)).

Figure 7:
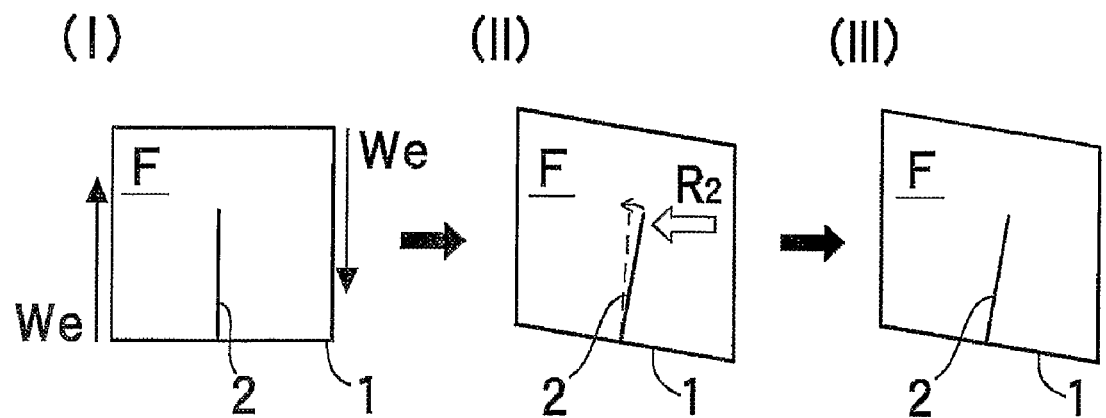
FIGS. 7(I) to (III) show deformation variation of the deformation sensing device receiving the shearing force in the We direction relative to the lapse of time.
Figure 8:
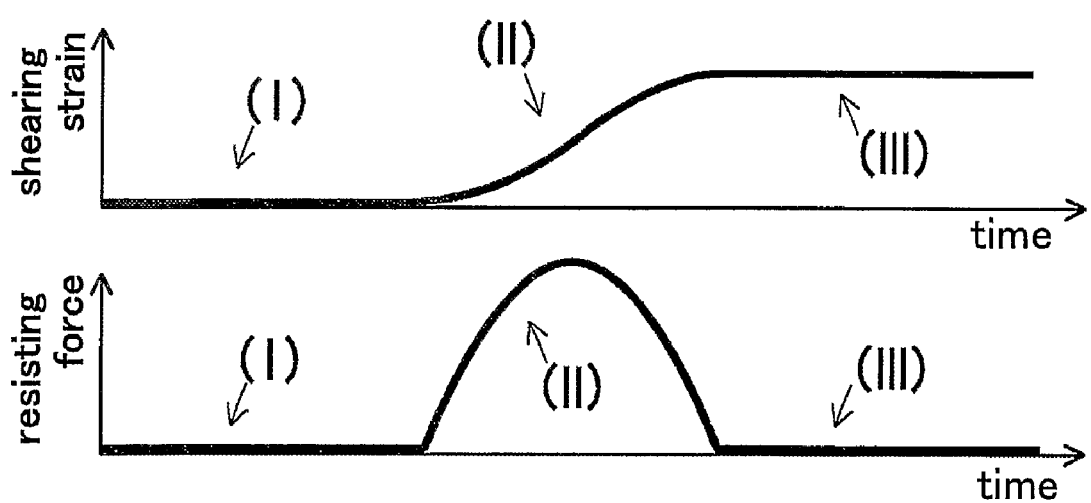
FIG. 8 shows the relation between the shearing force variation and the lapse of time when the shearing stress is applied to the deformation sensing device (upper figure), and shows the relation between the viscous resistance (resisting force) variation and the lapse of time when the shearing stress is applied to the deformation sensing device (lower figure)

As shown in FIG. 7(I), acting the shearing stress on the both side surfaces of the deformation sensing device in the arrow direction We deforms the capsule 1 to the state as shown in FIG. 7(II). To the relative movement sensing member 2 slanting in the capsule corresponding to deformation of the capsule 1, the viscous resistance in the arrow direction $R_2$ is applied from the viscous fluid F. Thus, receiving the viscous resistance resulted from relative movement of the viscous fluid, the relative movement sensing member 2 flexes as shown in FIG. 7(II) by the dotted line. Amount of the viscous resistance is gradually attenuated as the time passes (refer to FIG. 7(III)).

In the deformation sensing device sensing the shearing stress, the capsule is preferably made of material having at least the elasticity. The elastic modulus ranges 0.02 to 2000 MPa, and it varies depending on the usage and degree of deformation to be detected. When the capsule is used as the robot skin, the elastic modulus of 0.02 to 0.3 MPa is preferable.

Figure 9:
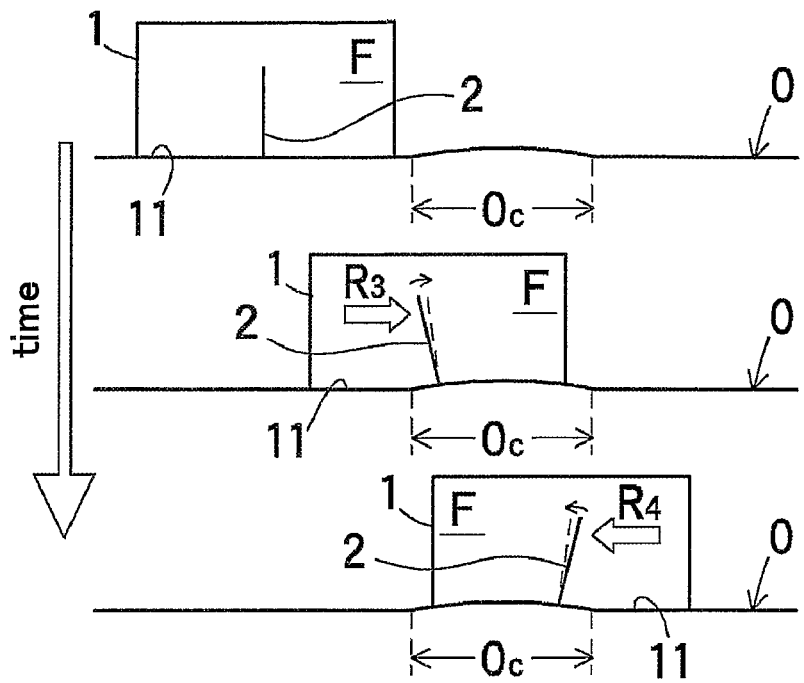
FIG. 9 shows deformation variation relative to the lapse of time when the deformation sensing device of FIG. 4 passes over the object to sense the convexo concave (upper, middle and lower figures)

FIG. 9 is an explanatory view showing a cross-section of the relative movement sensing member of FIG. 4 schematically. It senses movement of the viscous fluid flowing in the left-right direction in FIG. 9. With the deformation sensing device being contacted with the object surface, the deformation sensing device and the object are relatively moved. As the time passes, the capsule 1 deforms into the shape continuously following to property the object surface. Especially, the deformation sensing device in which the capsule 1 has a flexible sheet is convenient. By sliding the deformation sensing device so that the flexible sheet 11 follows to the object surface including a bulge portion Oc, the convexo concave of the object O can be detected.

In an initial state shown in an upper figure of FIG. 9, the deformation sensing device is put on the flat surface. Then, the deformation sensing device is slid rightward toward the bulge portion Oc following to the surface of object O by the predetermined speed, as shown in the middle figure. The relative movement sensing member 2 slants to be orthogonal to the tangential line of the bulge portion Oc, as shown in the middle figure and the lower figure. The viscous fluid F applies the viscous resistance in the direction shown by the arrows $R_3$ and $R_4$ to the relative movement sensing member 2. Receiving the viscous resistance, the relative movement sensing member flexes as shown by the dotted line in the middle and lower figure, to thereby sense movement of the viscous fluid.

The flexible sheet, used with being contacted with object surface, preferably has the flexibility (softness) to be flexed following to the surface shape of the object. The elastic modulus of the flexible sheet preferably ranges from 1000 to 3000 MPa, and it varies depending on the thickness thereof. For obtaining such range of the elastic modulus, the resin material such as PET, polyacetal, polycarbonate and acryl can be adopted.

The thickness of the flexible sheet preferably ranges from 0.1 to 2 mm, and it varies depending on the elastic modulus. The flexible sheet having the above elastic modulus and thickness can easily deform to follow the object surface, which is convenient to detection of the object convexo concave.

The flexible sheet can be made of the material so that the friction between the flexible sheet and the object is small. When this friction is small, the deformation sensing device can be slid smoothly on the object surface to easily detect the convexo concave. Even when the flexible sheet material makes the friction larger, other member which can reduce the friction but does not reduce flexibility of the flexible sheet may be disposed between the flexible sheet and the object. As such other member, a tape or film made of the material different from that of flexible sheet can be attached to the lower surface of the flexible sheet.

Using the material having the elasticity as well as the flexibility can realize the deformation sensing device having softness equivalent to the human skin. Thus, property of the object to be detected can be enlarged.

Plural deformation sensing devices disposed continuously can construct the deformation sensing device of the present invention. In this case, one wall of the first capsule can commonly be used as one wall of the second capsule. Concretely, the flexible body made of silicone rubber etc. is provided with plural cavities for containing the viscous fluid therein, and the relative movement sensing member therein. Disposing plural relative movement sensing member (plates) in plural capsules having different detecting directions enables to sense deformations in plural directions.

The relative movement sensing member preferably has an exhibiting tool that acts by sensing a relative movement against the viscous fluid. A light emitter emitting light depending on a result of sensing by the relative movement sensing member can be exemplified. Detected or sensed deformation exhibited by the emitted light can be visually observed or recognized. The color or intensity of the emitted light can be changed corresponding to degree of the detection.

Based on the detected result, the absolute value of amount of the acting stress and convexo concave can be calculated. By memorizing the plural detected result in the memory as a template in advance, the property of other object can be specified.

The inventor has conceived the deformation sensing device of the present invention through analysis of the Meissner's corpuscle construction. Therefore, the deformation sensing device is expected to detect the large stress when the human senses the large stress. There is possibility the standard of the convexo concave inspection for the steel plate etc. performed by the worker is quantified.

3. Convexo Concave Position Exhibiting Device

The convexo concave position exhibiting device of the present invention is comprised of a sensing-and-exhibiting member, and a controlling member.

The sensing-and-exhibiting member comprises a sensing portion and an exhibiting portion. The sensing portion comprises plural deformation sensing device of sensing a deformation thereof caused by a convexo concave of the object. The exhibiting portion comprises plural light emitters and located opposite to the sensing portion. The controlling member controls the light emitters to emit light depending on a result of sensing by the deformation sensing device.

In the sensing-and-exhibiting member, the sensing portion and the exhibiting portion are disposed by the front and rear relation. Accordingly, operator can visually recognize the detected position on the object surface by the emitted light of the exhibiting portion. Any position sensor for measuring the position where the convexo concave is detected need not be provided. When the convexo concave position exhibiting device is slid on the object surface in high speed so that the sensing portion sense the convexo concave, the exhibiting portions continuously emit the light corresponding to the detected convexo concave. The light of the light emitters remain in the operator's retina as the residual image of light, whereby the operator can visually recognize the convexo concave position on the object surface.

There is no restriction for the deformation sensing device of the sensing portion, so long as it can sense the object convexo concave by the relative movement between the sensing portion and the object surface. In addition to the conventional sensor such as the strain gauge and the PVDF sensor, the above mentioned convexo concave amplifying device and the deformation sensing device can be exemplified, as the deformation sensing devices. The plural deformation sensing devices can be arranged in the sheet-shape to form the sensing portion.

There is no restriction for the exhibiting portion, so long as it can emit the light. The light emitters which can emit the light of high visible characteristic sufficiently strongly, such as the light emitting diode, is preferably used.

The controlling member for causing the light emitter to emit the light preferably has the thresholds set in advance. Based on comparison of the threshold with the degree of detected convexo concave, it judges presence/absence of the convexo concave to control put-on/put-off of the light emitter. By changing the value of threshold, sensitivity of convexo concave position exhibiting device can be adjusted arbitrarily. The color and intensity of the emitted light of the light emitter can be changed corresponding to the detected degree.

There is no restriction of the material and shape for the sensing portion and the exhibiting portion. They preferably have sheet shape. The sensing portion contacting with the object surface preferably has the softness to follow to the object surface. Concretely, the resin sheet such as the nylon and vinyl, and the fiber sheet such as the fabric and felt can be exemplified.

The sensing-and-exhibiting member preferably has the shape so that the operator can use it by the hand. It can have the bag-shape in which the sensing portion positions at the palm side of hand, while the exhibiting portion positions at the back side of hand. For example, arranging the deformation sensing device and the light emitters respectively at the palm side and the back side of the bag-shaped body such as the work glove and the vinyl glove hand can realize the portable sensing-and-exhibiting member.

There is no restriction of arrangement of the deformation sensing device so long as it is fixed to one surface of the sensing portion. Plural deformation sensing devices can be arranged at random on the sensing portion by the predetermined pattern to cover the whole surface of it, or by the predetermined intervals. The plural deformation sensing devices are preferably arranged in the same pattern as the plural light emitters mentioned above. The controlling member preferably has a controlling portion to cause some of the light emitters, arranged in the same pattern as the plural deformation sensing devices, to emit the light. Thus, the light emitter corresponding to the deformation sensing device having detected the convexo concave, emits the light to exhibit the convexo concave position accurately.

4. Convexo Concave Position Exhibiting Method

The convexo concave position exhibiting method of the present invention is comprised of a relative moving step, a detecting step and an exhibiting step.

In the relative moving step, the deformation sensing device and the object are moved relatively on the condition that the deformation sensing device is contacted with a surface of the object. The detecting step detects the convexo concave by that the deformation sensing device senses a deformation thereof caused by a convexo concave of the object. The relative movement makes the position detection of convexo concave in larger area possible.

There is no restriction of deformation sensing device so long as it can detect the convexo concave on the object. In addition to the conventional sensors such as the strain sensor and the PVDF sensor, the convexo concave amplifying device mentioned above can be exemplified. For carrying out the convexo concave detecting step, the deformation sensing device and the convexo concave position exhibiting device above mentioned can be used. The deformation sensing device contacted with the object surface is preferably slid or moved. The deformation sensing device can be slid relative to the object mechanically, but sliding it manually is preferable.

In the exhibiting step, the position of convexo concave on the object surface is time-dependently exhibited by emitting light depending on the detected result in the relative moving step and the detecting step. Thanks to the time-dependent light emission, position of the convexo concave can be accurately judged.

The convexo concave position exhibiting method can additionally include a judging step. It judges presence/absence of the exhibiting in the exhibiting step, based on the degree of convexo concave detected in the relative moving step and the detecting step. When the convexo concave position exhibiting method is applied to the surface inspection of the steel plate, the judging step contributes to find out the bad or rough surface by the predetermined surface accuracy.

In the exhibiting step, a position of a convexo concave on a surface of the object is preferably exhibited on the surface of the object by emitting light at the position where the convexo concave exists. The exhibiting step preferably exhibits (emits light) at the position just above the object convexo concave. Arranging the light emitter at the same position as the deformation sensing device enables the operator to visually recognize the accurate position of the convexo concave.

For carrying out the convexo concave position exhibiting method, the deformation sensing device having the light emitter as a exhibiting tool, and the convexo concave position exhibiting device above mentioned can be used. In sliding the convexo concave position exhibiting device on the object surface, the plural light emitters emit the light continuously, whereby the operator can visually recognize position of the convexo concave.

One example of the convexo concave position exhibiting method of the present invention will be explained with reference to FIGS. 10 and 11. Left part of FIG. 10 shows the back side of hand of the convexo concave position exhibiting device, while right part shows the palm side of hand of it. FIG. 11 shows the convexo concave position exhibiting method using the convexo concave detected position exhibiting device.

The sensing-and-exhibiting member 50 preferably has the bag-shape including two sheets 51 and 52 each having the shape of human hand shape. The operator can wear the sensing-and-exhibiting member 50 on the hand. The sheet 51 (sensing portion) positioned at the palm side of hand is provided with plural sensors S' as the deformation sensing device on an outer surface thereof by the constant interval. When the detecting area is extended in one direction, the plural sensors which sense same direction are arranged on the line. When the sensors S' are comprised of the above deformation sensing device, they are preferably arranged in the direction extending from a wrist to fingertip. By moving the sensing-and-exhibiting member 50 in the direction where the sensors are arranged, the convexo concave can be detected (to be explained later).

On the sheet 52 (exhibiting portion) positioned at the back side of hand is preferably provided with plural light emitters L' on an outer surface thereof. The light emitters L' preferably comprised the exhibiting portion, are arranged by the same mode of the sensors S'.

The light emitters L' corresponding to the sensors S' having detected the convexo concave are to be lighted. Some of the sensors and some of the light emitters are added reference $S_1'$ to $S_{15}'$, and $L_1'$, to $L_{15}'$ in FIG. 10. Sn' on the palm side of hand (sheet 51) and Ln' on the back side of hand (sheet 52) are corresponded to each other. For example, when the sensor $S_1'$ detects the convexo concave, the light emitter $L_1'$ emits the light. The sensor $S_1'$, $S_2'$ - - - and the light emitters $L_1'$, $L_2'$ - - - operate similarly.

In detecting the object convexo concave, the operator wears the sensing-and-exhibiting member 50 on the right hand, for example. The sensing-and-exhibiting member 50 is moved, with the sheet 51 being contacted with the object surface, in the direction from the fingertip to the wrist as shown by the arrow in FIG. 11. Plural light emitters L' are put on/off continuously. Here, the light emitters L' passing over the convexo concave emit the light (refer to the mark E), which enables the operator to visually recognize the position of convexo concave.

Even when the sensing-and-exhibiting member 50 is slid quickly, the residual image of light remaining on the operator retina makes the position recognition possible.

Preferred Embodiment 1. 1st Embodiment

Figure 12:
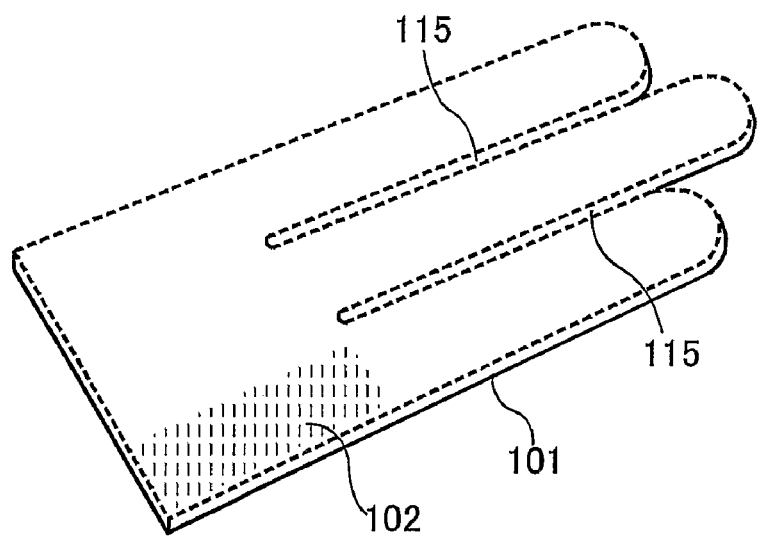
FIG. 12 is a concept view showing the whole convexo concave amplifying device of the embodiment 1.
Figure 13:
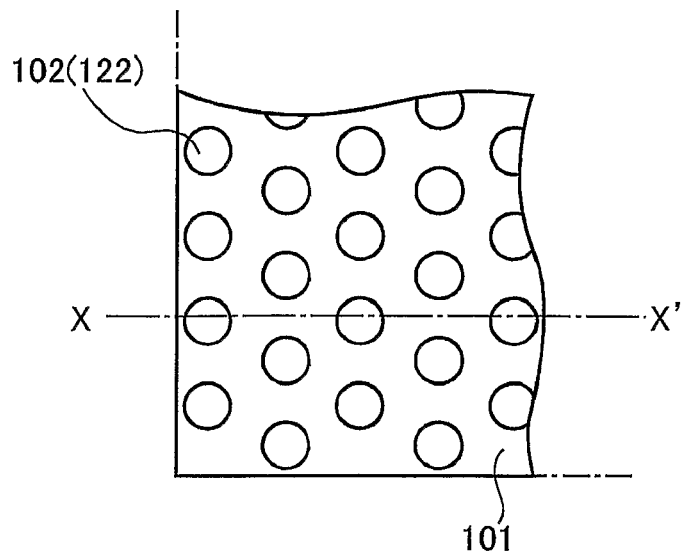
FIG. 13 is an enlarged plan view of the convexo concave amplifying device of FIG. 12.

An embodiment of a convexo concave amplifying device of the present invention will be explained with reference to FIGS. 12 to 15. FIG. 12 show the whole convexo concave amplifying device of the embodiment, FIG. 13 is a partially enlarged plan view of the same FIG. 14 is a cross-section along line X-X' in FIG. 13, and FIG. 15 is an explanatory view for explaining convexo concave detection by the convexo concave amplifying device.

The convexo concave amplifying device is comprised of a sheet-like base portion 101 operating as the sensing member, and plural protrusions 102 formed integral with the base portion 101 to operate as the exhibiting member 120.

The base portion 101 has the thickness of 0.3 mm, the width of 60.0 mm, and length (max.) of 133.5 mm. Two slits 115 extending longitudinally from one end are formed in parallel (refer to FIG. 12). Thus, the base portion 101 is divided into the first portion, second portion and third portion on which the forefinger, the middle finger and the ringfinger are rested respectively. For operation, the convexo concave amplifying device is pushed by the fronts of three fingers and the central portion of the palm of hand.

Figure 14:
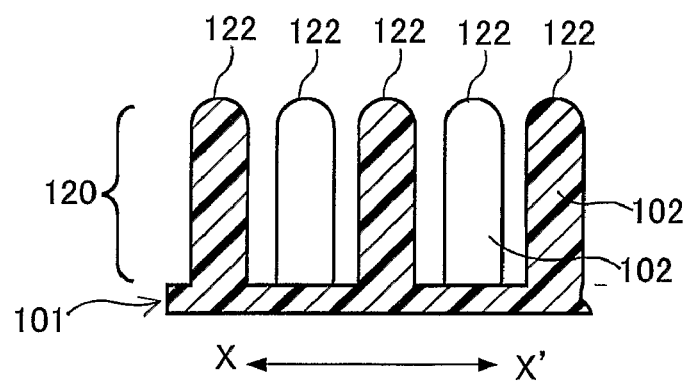
FIG. 14 is a cross-sectional view along a line X-X' in FIG. 13.
Figure 15:
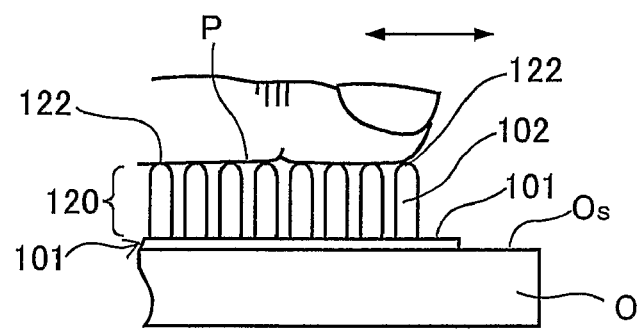
FIG. 15 partially shows detecting manner for detecting the object convexo concave by the convexo concave amplifying device of the embodiment 1.

The plural protrusions 102 are formed on an upper surface as a whole (refer to FIG. 14). They are positioned at the cross points of the triangular grids of which side has length of about 1.7 mm. Each protrusion 102 has a small column shape of which diameter is 1 mm and height is 3.2 mm, and upstanding in the thickness direction of the base portion 101. The top portion of the protrusion has a semispherical shape of which diameter is 1 mm.

The convexo concave amplifying device having the base portion 101 and the plural protrusions 102 is made of the photo-curing resin of which elastic modulus is 2400 MPa and formed by the stereolithography device. On a lower surface of the base portion 101, a tape (not shown) for reducing the friction is attached.

Next, the detecting method for detecting a surface Os of the object O by the above convexo concave amplifying device will be explained, with reference to FIG. 15 which only shows the top portion of the convexo concave amplifying device. Convexo concave is detected at the remaining portion of the finger, and the palm of the hand similarly.

In the detecting, the base portion 101 is pressed onto the surface Os of object O, and the finger front P is pressed onto the protrusions 102. The finger is moved in the arbitrary direction (in the arrow direction in FIG. 15), to slide the convexo concave amplifying device on the surface Os. Being pressed by the normal tracing force, the base portion 101 bends following to the shape of surface Os. As a result, deformation occurs at the tip ends 122 of the protrusion 102, corresponding to shape variation of the surface Os.

For detecting the convexo concave by the finger and the palm, the convexo concave amplifying device is pressed onto the object surface by the pressure of 0.01 to 0.02 MPa, and is reciprocately slid by the speed of 100 mm/sec.

Evaluation

Plural persons (A to G) carried out the detection by the above convexo concave amplifying device. On the upper surface of sample object, the convex having the height of 0.04 mm and the diameter of 10 mm is formed. As the comparison sample, detecting test is carried out similarly by the film made of polyethylene having the thickness of 0.013 mm. In the Table 1 showing the test result, the mark ◎ means clear detection of the convex, and the mark ○ means barely detection of the same. The mark x means no convex can be detected.

TABLE 1

|  | A | B | C | D | E | F | G |
|---|---|---|---|---|---|---|---|
| Comparative Sample | X | ○ | ○ | X | X | X | X |
| Embodiment | ◎ | ◎ | ◎ | ◎ | ◎ | ◎ | ◎ |

As apparent from the Table 1, the convexo concave amplifying device of the embodiment can easily and clearly detect the convex which can be hardly detected by the polyethylene film. According to the simulation using the finite element method (FEM), the time dependent variation of strain transmitted to the Meissner's corpuscle in the shearing direction is amplified by 20 times by the convexo concave amplifying device, compared with the case by the bare hand.

The skilled workers having the excellent tactile sensing carried out the surface inspection test of the steel plate by using the convexo concave amplifying device. They commented "sensitivity seems to be amplified clearly", "small strain conventionally overlooked can be detected", "the work glove requires many times tracing but bringing unclear feeling, whereas the convexo concave amplifying device brings clear sensing only by few times tracings", and "small pressing force of the convexo concave amplifying device can reduce the fatigue".

2. 2nd Embodiment

Figure 16:
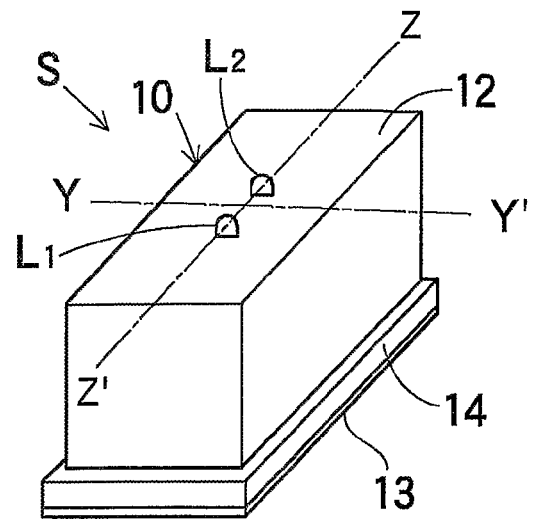
FIG. 16 is a perspective view of the deformation sensing device of the embodiment 2.
Figure 17:
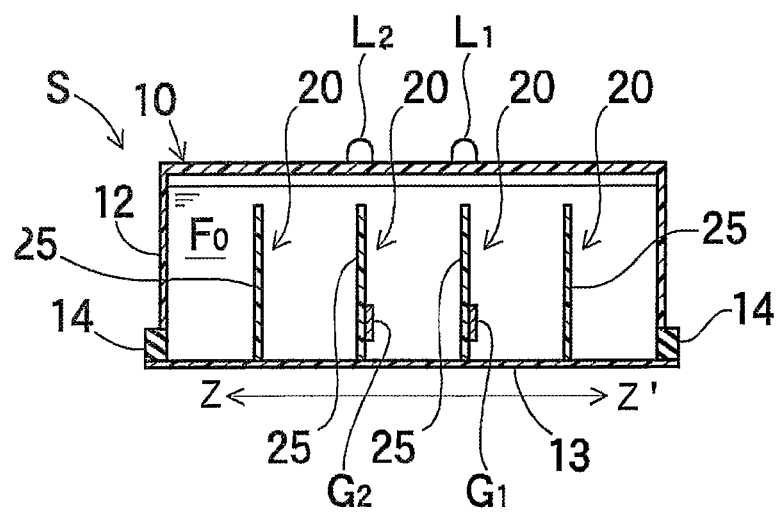
FIG. 17 (upper figure) is a cross-sectional view along a line Z-Z' in FIG. 16, and a cross-sectional view along a line Y-Y' in FIG. 16 (lower figure)
Figure 17:
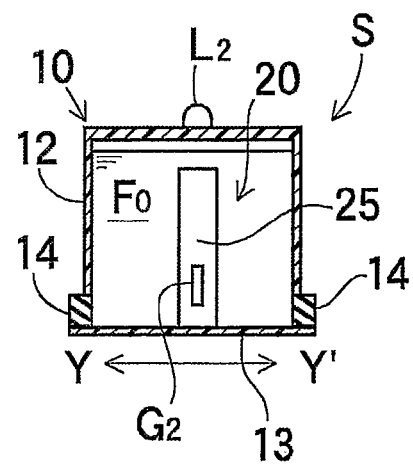
Figure 18:
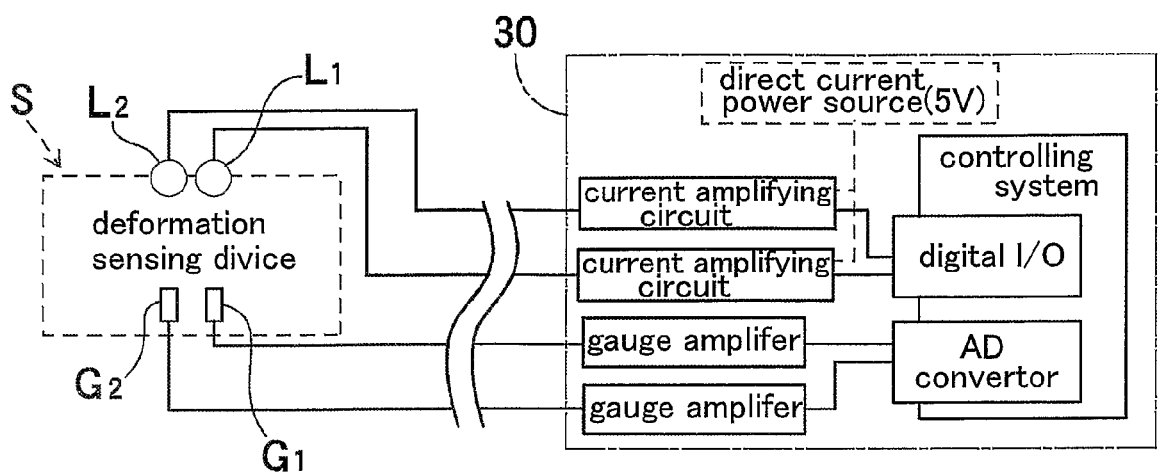
FIG. 18 is an explanatory view for explaining the controlling system used for the deformation sensing device of the embodiment 2.

Next, the 2nd embodiment of the deformation sensing device will be explained with reference to FIGS. 16 to 18. FIG. 16 is a perspective view of the deformation sensing device, upper figure and a lower figure of FIG. 17 are respectively cross-sections along a line Z-Z' and a line Y-Y' in FIG. 16. FIG. 18 is a view for explaining a controlling system controlling the deformation sensing device.

The deformation sensing device is comprised of a capsule 10 containing a viscous fluid, and a relative movement sensing member 20. The capsule 10 has the hexahedron structure of which width, length and height are 37 mm, 62 mm and 37 mm, respectively. It includes a box-shape case 12 made of polypropylene (elastic modulus: 1600 MPa) and has thickness of 1.5 mm, and a plate-shape bottom portion 13 made of acryl (elastic modulus: 2500 MPa) and has thickness of 0.5 mm. The silicone oil Fo (dynamic viscosity: $1 \times 10^5$ mm$^2$/sec) is contained in the capsule 10. Abutted portion between the case 12 and the bottom portion 13 is sealed by the annular seal 14 made of hard rubber.

The relative movement sensing member 20 includes plural fin 25, and strain gauges $G_1$ and $G_2$. Each fin 25 is made of acryl (elastic modulus: 2500 MPa) and has plate shape. Width, length and thickness are respectively 9 mm, 23 mm and 0.5 mm. Four fins 25 are attached to the bottom portion 13 by the conventional adhesive agent. They are arranged by the constant interval in parallel, to be flexed in the Z-Z' direction. On the two fins 25 locating at middle area, the strain gauges $G_1$ and $G_2$ are fixed at the root portion thereof.

On an upper surface of a roof portion of the case 12, two light emitters (light emitting diodes) $L_1$ and $L_2$ are fixed. Put-on/put-off of the light emitters $L_1$ and $L_2$ is controlled corresponding to the detected result by the strain gauge $G_1$ and $G_2$ by the controlling system 30 shown in FIG. 18. The controlling system 30 includes a calculating portion comprised of an electronic computer on which the controlling software and the input-output base plate are installed. The resistance of the strain gauges $G_1$ and $G_2$ taken out by the gauge amplifier are inputted as the voltage value to the calculating portion. The voltage value is then put into the digital signal by the A/D convertor to be processed at the calculating portion. By the switching of signal from the digital I/O corresponding to the processed result, the light emitters $L_1$ and $L_2$ are put-on/put-off, via current amplifying circuits amplifying 5V of a direct current power source.

In detecting the convexo concave, the deformation sensing device S is slid. Thanks to the acceleration thus generated, inertia of the silicone oil Fo influences to the fin 25. The controlling system 30 separates only the signal regarding the deformation by the calculation and processing. That is, signal resulting from the acceleration is transmitted to the light emitters $L_1$ and $L_2$ simultaneously, while the signals from the strain gauges $G_1$ and $G_2$ detecting the convexo concave are transmitted to the light emitters $L_1$ and $L_2$ by the time difference. The light emitter $L_1$ is set to put on when the strain gauge $G_2$ and the strain gauge $G_1$ receive the signals in this order, while the light emitter $L_2$ is set to put on when the strain gauge $G_1$ and the strain gauge $G_2$ receive the signals in this order.

(Detecting Mode 1)

Figure 19:
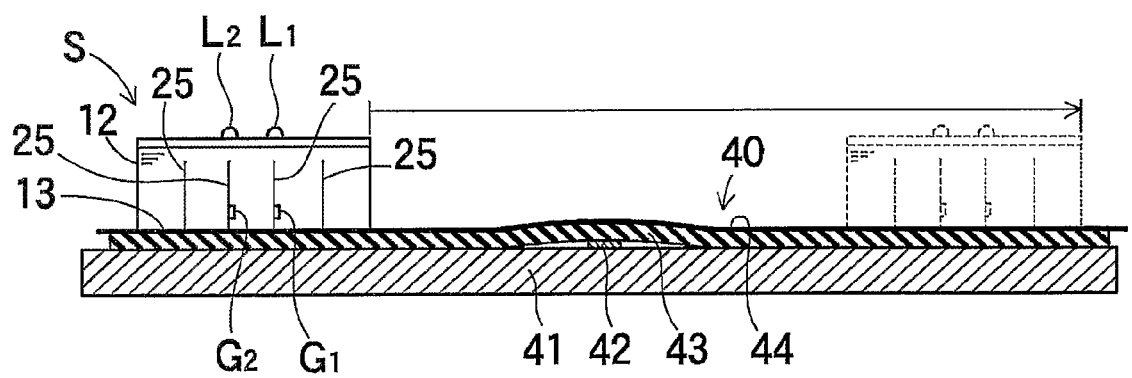
FIG. 19 is an explanatory view showing the detecting test of the detecting modes 1 and 2.
Figure 20:
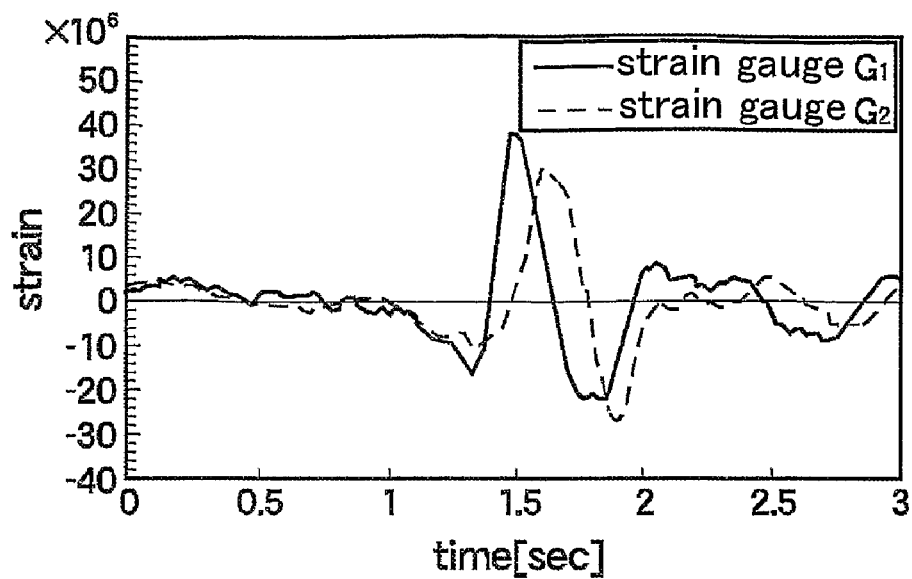
FIG. 20 is a graph showing the strain variation relative to the lapse of time occurred in the strain gauge in the detecting mode 1.

The test of the object convexo concave was carried out by the above deformation sensing device S of the Embodiment 2. Detail of the test will be explained with reference to FIG. 19. A detected body 40 was prepared as below. A circular sheet 42 having thickness of 0.09 mm and diameter of 4 mm is putted on an acryl plate 41, and the sheet 42 is covered by a rubber sheet 43 of chloroprene.

Thus, the detected surface having the moderate convex surface was prepared. Further, the rubber sheet 43 was coated by a sheet made of polyethylene and having thickness of 0.06 mm to reduce the friction between the deformation sensing device S and the detected surface.

In the detection test, the case 12 of the deformation sensing device S is held by the operator's hand so that the bottom portion 13 is abutted onto the detected surface. The deformation sensing device S is moved rightward as shown by arrow, over the convex surface by the speed that it traveled 25 mm by 3 second. When the deformation sensing device S passes on the convexed detected surface, the light emitter L1 is put on and then put off, but the light emitter L2 was not put on. To the contrary, when the deformation sensing device S passes on the convexed detected surface in the reverse direction, the light emitter L2 is put on and then put off, but the light emitter L1 was not put on.

In this way, the operator visually recognized the position of detected position. Further, even when the deformation sensing device S is moved quickly, the operator recognized the convex position by the residual image of light remained on the retina.

(Detecting Mode 2)

Figure 21:
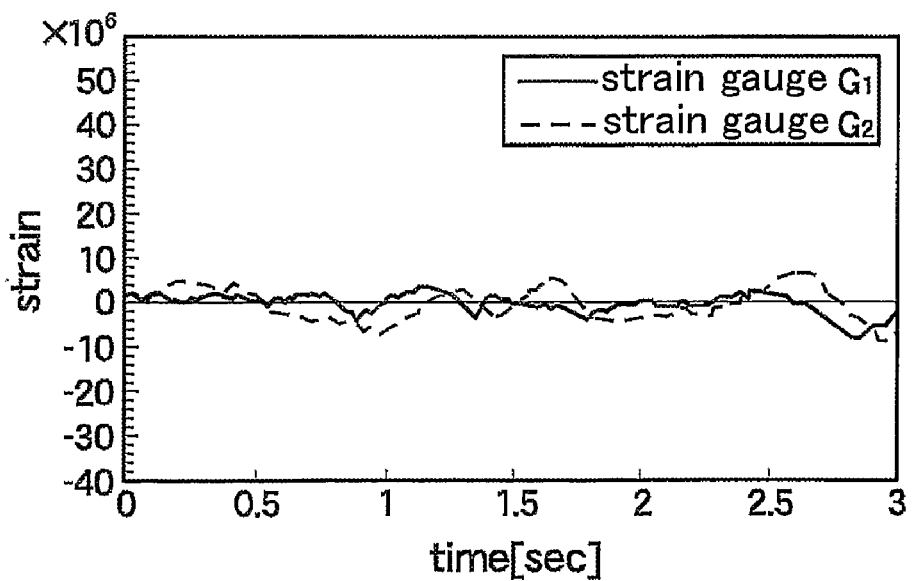
FIG. 21 is a graph showing the strain variation relative to the lapse of time occurred in the strain gauge in the detecting mode 2.

The detecting mode 2 was carried out in the same way as mentioned, after removing the circular sheet 42 on the detected body 40 of the detecting mode 1. As a result, none of the light emitters L1 or L2 did not emit the light. The time dependent deformation variation is shown in FIG. 21. As apparent, large strain variation did not occur in any of the strain gauge G1 or G2. It is assumed no prominent deformation was generated due to removal of the circular sheet 42.

The invention claimed is:

1. A convexo concave amplifying device for exhibiting a convexo concave by amplifying a sense of a convexo concave of an object, comprising:
    a sensing member comprising a flexible sheet able to contact with the surface of the object and to deform concavely and convexly along the surface of the object; and
    an exhibiting member that is formed on a surface of the flexible sheet and has a deformation resistance smaller than that of the flexible sheet in at least one of a plurality of directions orthogonal to a direction of thickness of the flexible sheet,
    wherein the exhibiting member comprises a plurality of protrusions formed directly on a surface of the sensing member.

2. A convexo concave amplifying device according to claim 1, wherein the exhibiting member comprises plural protrusions separated equidistantly and formed on the surface of the flexible sheet.

3. A convexo concave amplifying device according to claim 2, wherein the protrusions are plates parallel to each other.

4. A convexo concave amplifying device according to claim 2, wherein the protrusions are columns.

5. A convexo concave amplifying device according to claim 1, wherein the exhibiting member is made of foam.

6. A convexo concave amplifying device according to claim 1, wherein the exhibiting member is a sheet having plural holes extending in a direction of thickness thereof.

7. A convexo concave amplifying device according to claim 1, wherein the sensing member or the exhibiting member is made of resin.

8. A convexo concave amplifying device according claim 1, wherein the exhibiting member further comprises a strain sensing tool for detecting a strain of the exhibiting member.

9. A convexo concave amplifying device according to claim 8, wherein the strain sensing tool is a strain gauge.

10. A convexo concave detecting method for detecting a convexo concave of an object, comprising
    a process of using a convexo concave amplifying device comprising a sensing member comprising a flexible sheet and an exhibiting member that is formed on a surface of the flexible sheet and has a deformation resistance smaller than that of the flexible sheet in at least one of a plurality of directions orthogonal to a direction of thickness of the flexible sheet, wherein the process comprises
    a contacting step of contacting the sensing member with a surface of the object and deforming the flexible sheet of the sensing member concavely and convexly along the surface of the object, and
    a detecting step of detecting the convexo concave by sensing a deformation of the exhibiting member induced in the contacting step, wherein the exhibiting member comprises a plurality of protrusions formed directly on a surface of the sensing member.

11. A convexo concave detecting method according to claim 10, wherein
the convexo concave amplifying device in contact with the surface of the object is slid in the contacting step, thereby an amount of the deformation of the exhibiting member is induced to depend on time, and
a variation of a time-dependent amount of the deformation of the exhibiting member is sensed by a tactile sense in the detecting step.

12. A convexo concave detecting method according to claim 10, wherein the object comprises:
a surface portion having flexibility; and
a convexo concave portion having a convexo concave covered by the surface portion, wherein
the flexible sheet is pressed onto the surface of the object and is deformed along the surface of the object in the contacting step, and the convexo concave of the convexo concave portion is detected in the detecting step.

13. A convexo concave amplifying device according to claim 1, wherein said sensing member has a thickness, and said exhibiting member includes a surface capable of inclination and a plurality of protrusions, said protrusions inclining in a tangential direction that is proportional to a product of an inclined angle $\theta$ of the surface when the surface is inclined and a thickness T of the convex concave amplifying device, wherein said thickness T corresponds to a sum of the thickness of the sensing member and a length of the protrusions.

14. A convexo concave detecting method according to claim 10, wherein said sensing member has a thickness, and said exhibiting member includes a surface capable of inclination and a plurality of protrusions, said protrusions inclining in a tangential direction that is proportional to a product of an inclined angle $\theta$ of the surface when the surface is inclined and a thickness T of the convex concave amplifying device, wherein said thickness T corresponds to a sum of the thickness of the sensing member and a length of the protrusions.

* * * * *